United States Patent
Rastegar et al.

(10) Patent No.: US 9,615,975 B2
(45) Date of Patent: Apr. 11, 2017

(54) SHAPE AND PRESSURE ADJUSTABLE DRESSING

(75) Inventors: Jahangir S. Rastegar, Stony Brook, NY (US); Thomas Spinelli, Northport, NY (US)

(73) Assignee: OMNITEK PARTNERS LLC, Ronkonkoma, NY (US)

( * ) Notice: Subject to any disclaimer, the term of this patent is extended or adjusted under 35 U.S.C. 154(b) by 391 days.

(21) Appl. No.: 13/230,797

(22) Filed: Sep. 12, 2011

(65) Prior Publication Data

US 2012/0238931 A1 Sep. 20, 2012

Related U.S. Application Data

(63) Continuation-in-part of application No. 13/046,767, filed on Mar. 13, 2011, now Pat. No. 8,604,266, which is a continuation-in-part of application No. 12/983,314, filed on Jan. 2, 2011, now Pat. No. 8,637,726.

(51) Int. Cl.
 *A61F 13/02* (2006.01)
 *A61F 13/00* (2006.01)
 *A61B 17/08* (2006.01)
 *A61B 17/00* (2006.01)

(52) U.S. Cl.
 CPC ........ *A61F 13/0233* (2013.01); *A61F 13/023* (2013.01); *A61F 13/0246* (2013.01); *A61B 17/083* (2013.01); *A61B 17/085* (2013.01); *A61B 2017/00867* (2013.01); *A61F 2013/0028* (2013.01); *A61F 2013/00119* (2013.01)

(58) Field of Classification Search
 CPC ......... A61B 17/085; A61F 2013/00119; A61F 2013/00165; A61F 2013/00238; A61F 2013/0028; A61F 13/025; A61F 13/02
 USPC ............ 602/41-44, 52, 54, 58; 606/215-216
 See application file for complete search history.

(56) References Cited

U.S. PATENT DOCUMENTS

| | | | |
|---|---|---|---|
| 4,605,005 A | 8/1986 | Sheehan | |
| 4,706,661 A * | 11/1987 | Barrett | A61B 17/085 606/215 |
| 4,815,468 A | 3/1989 | Annand | |
| 4,865,026 A * | 9/1989 | Barrett | A61F 13/00 128/857 |
| 5,630,430 A | 5/1997 | Shultz et al. | |
| 6,306,485 B1 | 10/2001 | Keller | |
| 6,838,589 B2 | 1/2005 | Liedtke et al. | |

(Continued)

OTHER PUBLICATIONS

Non-Final Office Action issued on related U.S. Appl. No. 11/998,926 issued on Jan. 21, 2009.

(Continued)

*Primary Examiner* — Kari Petrik

(57) ABSTRACT

A method for applying pressure to skin with a dressing. The method including: adhering at least a portion of the dressing to the skin; and subsequent to the adhering, changing the shape of the dressing by removing a restraint which restrains an elastic member associated with the dressing into a first shape. Where the removing of the restraint from restraining the elastic member moves the elastic member towards an unrestrained second shape to one or more of elongate or reduce a dimension of the dressing to apply a pressure to corresponding portions of the skin.

30 Claims, 25 Drawing Sheets

(56) References Cited

U.S. PATENT DOCUMENTS

| | | | |
|---|---|---|---|
| 6,849,057 B2 * | 2/2005 | Satou | A61F 13/0273 |
| | | | 602/41 |
| 6,916,967 B2 | 7/2005 | Wright et al. | |
| 7,122,712 B2 | 10/2006 | Lutri et al. | |
| 7,834,232 B2 | 11/2010 | Rastegar et al. | |
| 2003/0150449 A1 | 8/2003 | Spinelli et al. | |
| 2007/0282236 A1 | 12/2007 | LaGreca | |
| 2008/0146982 A1 | 6/2008 | Rastegar et al. | |
| 2008/0167593 A1 | 7/2008 | Fleischmann | |
| 2008/0306456 A1 | 12/2008 | Riesinger | |
| 2010/0318052 A1 | 12/2010 | Ha et al. | |

OTHER PUBLICATIONS

Final Office Action issued on related U.S. Appl. No. 11/998,926 issued on Oct. 13, 2009.
International Search Report Dated Dec. 4, 2012 received in corresponding International Application No. PCT/GB2012/052256.
International Search Report Dated Dec. 4, 2012 received in corresponding International Application No. PCT/GB2012/052258.

* cited by examiner

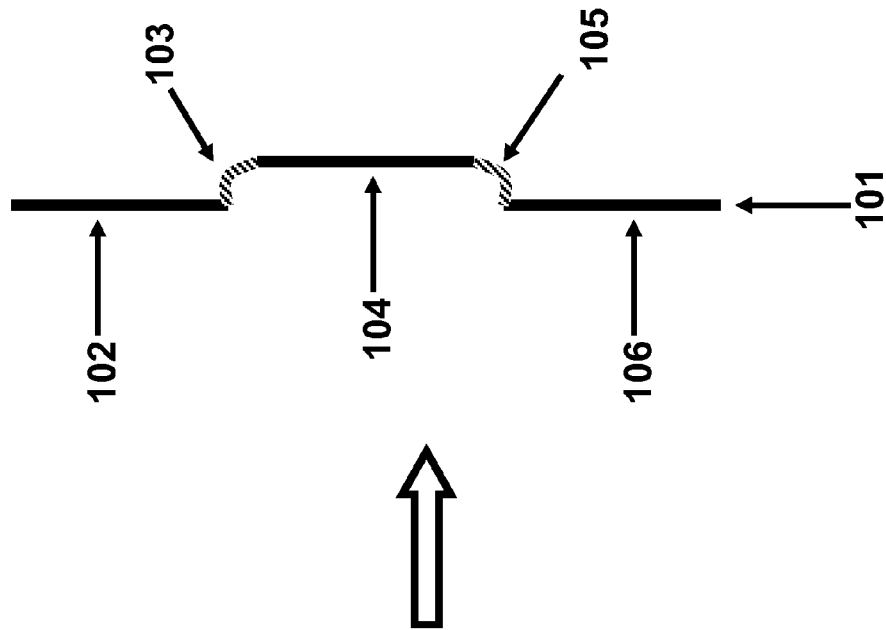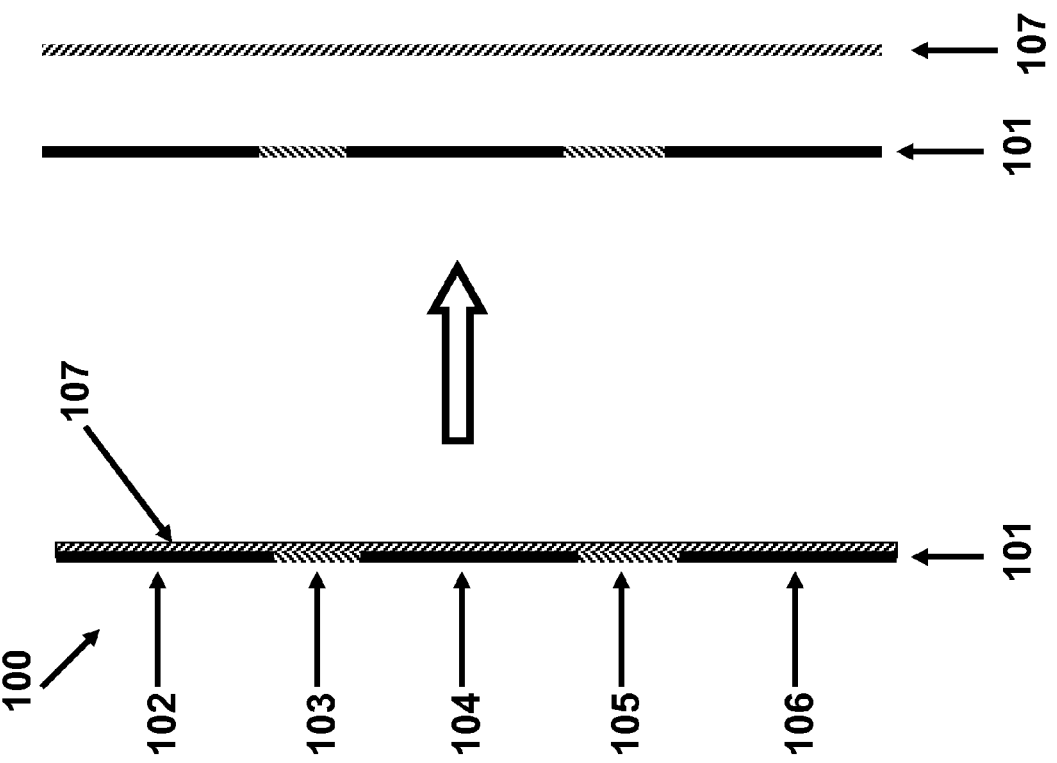

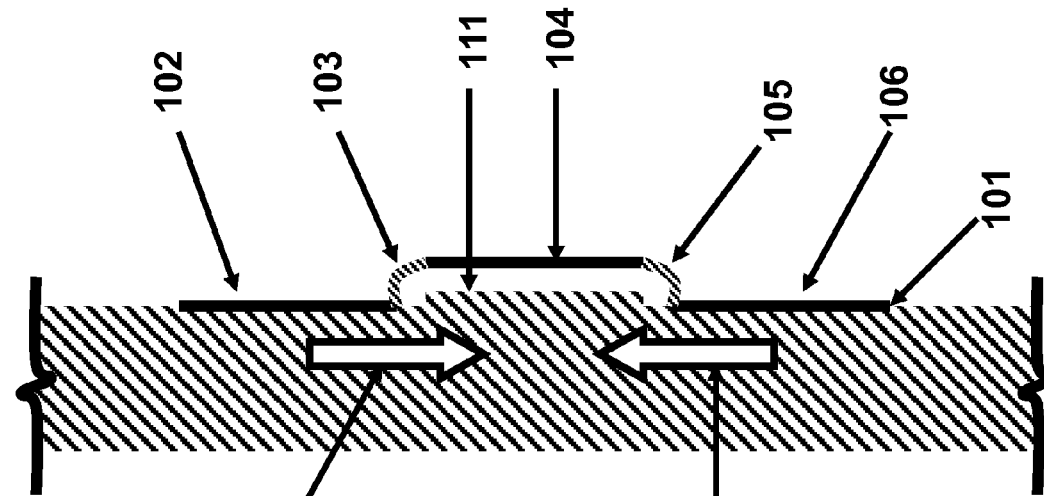
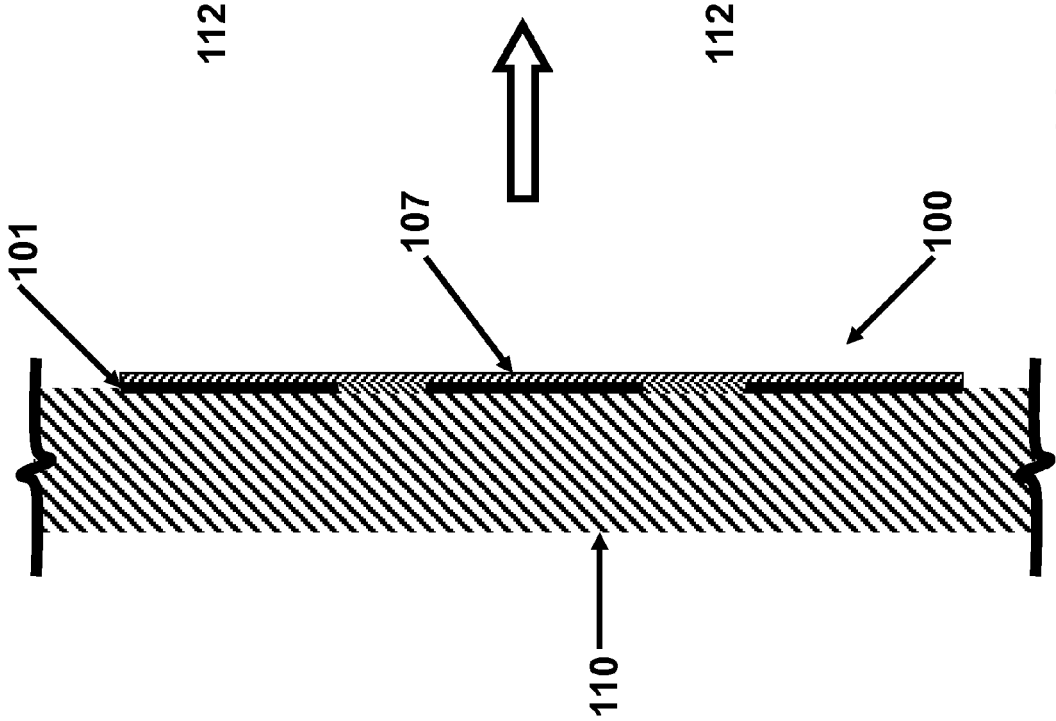

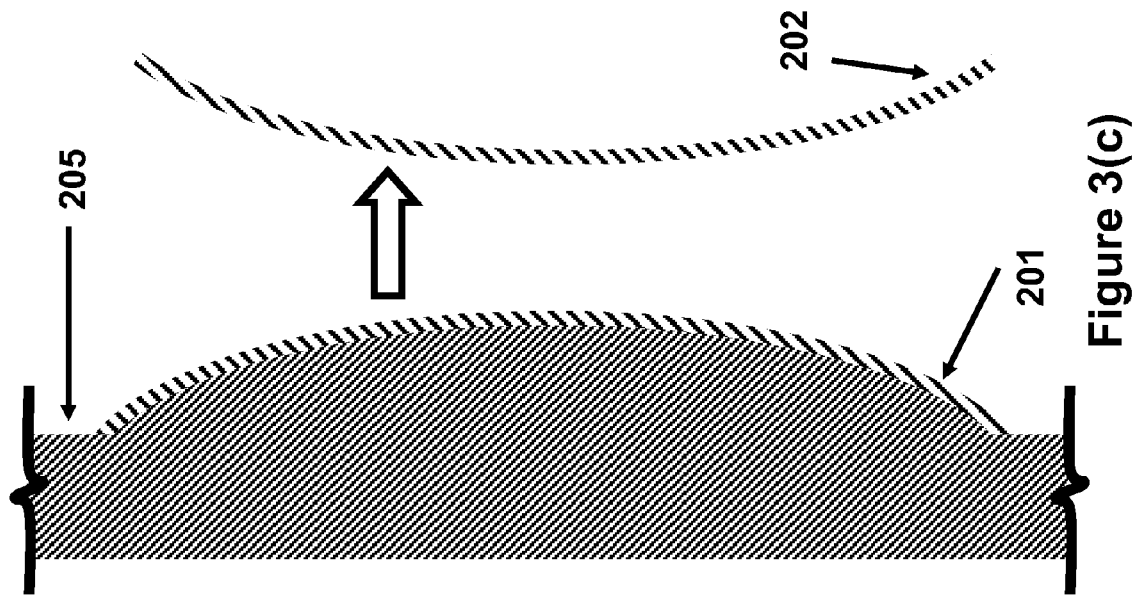
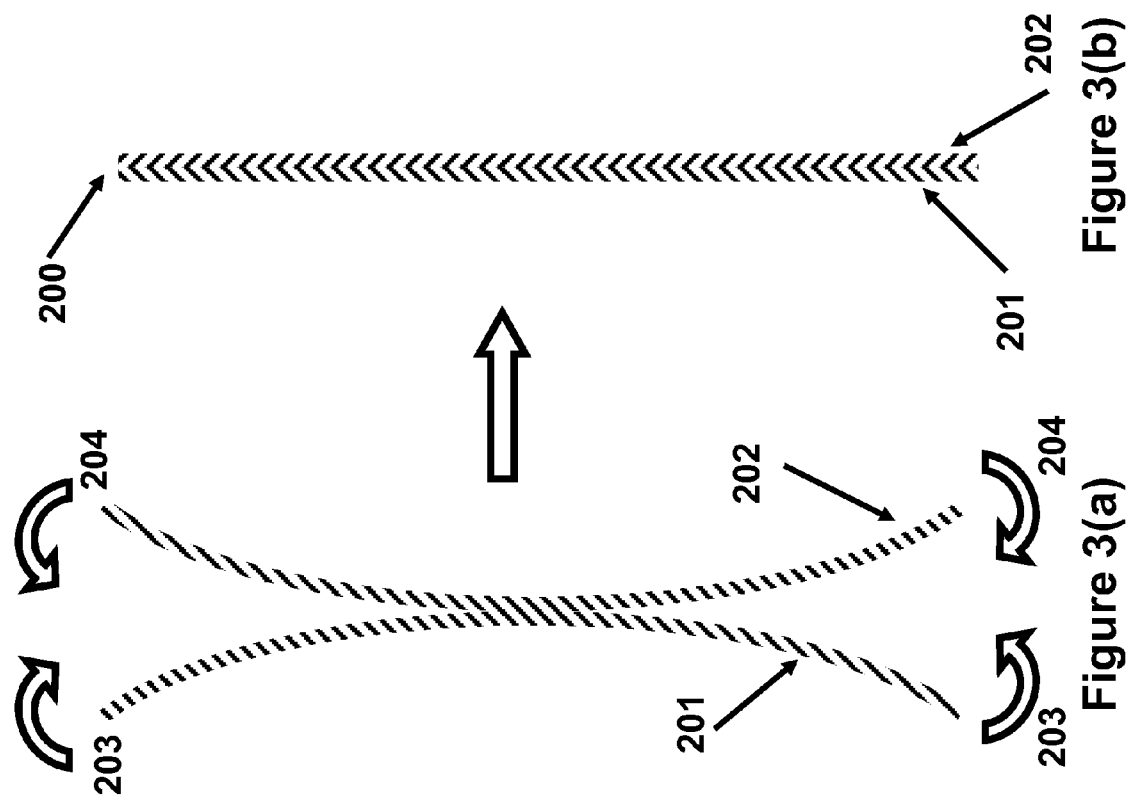

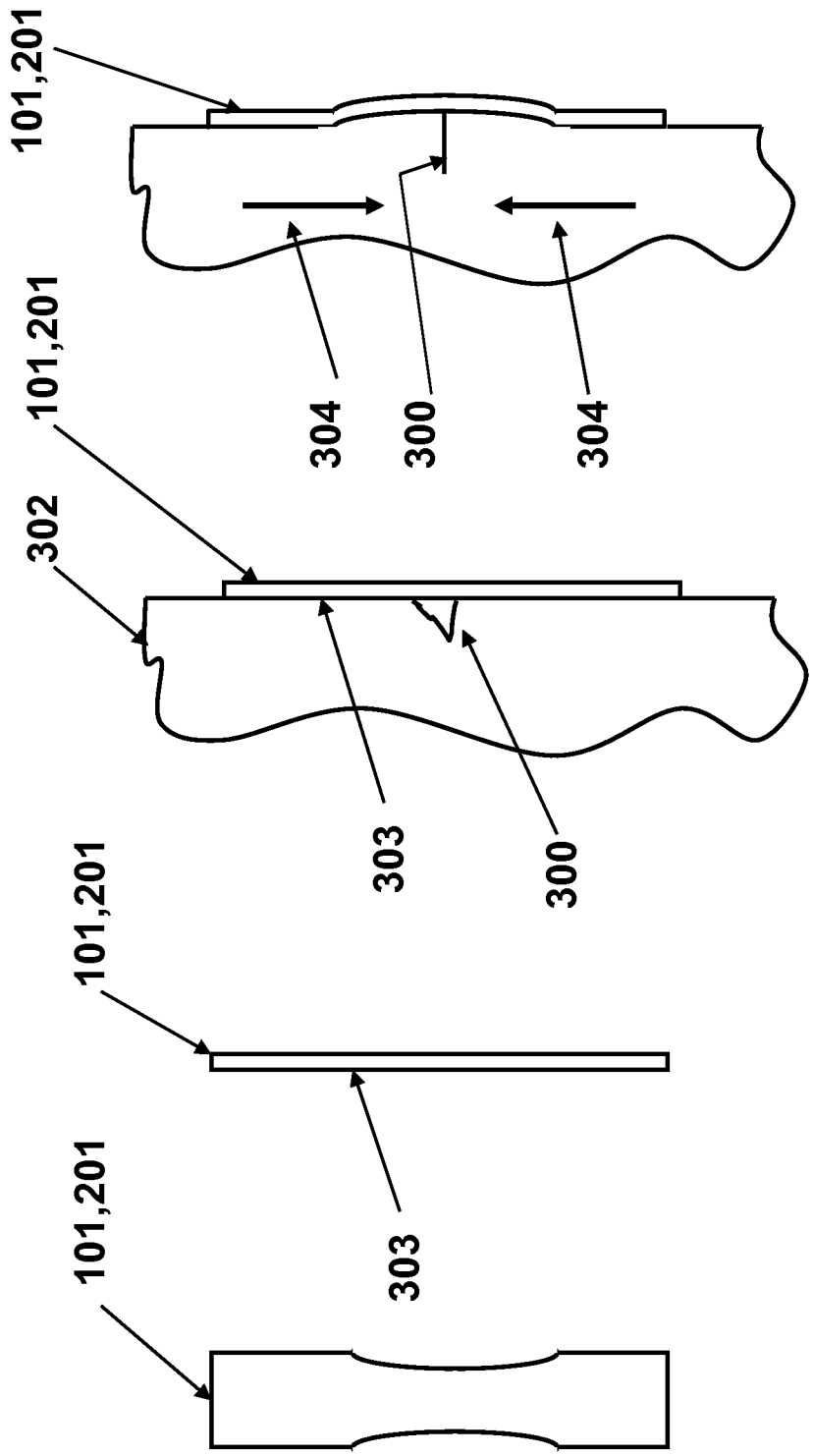

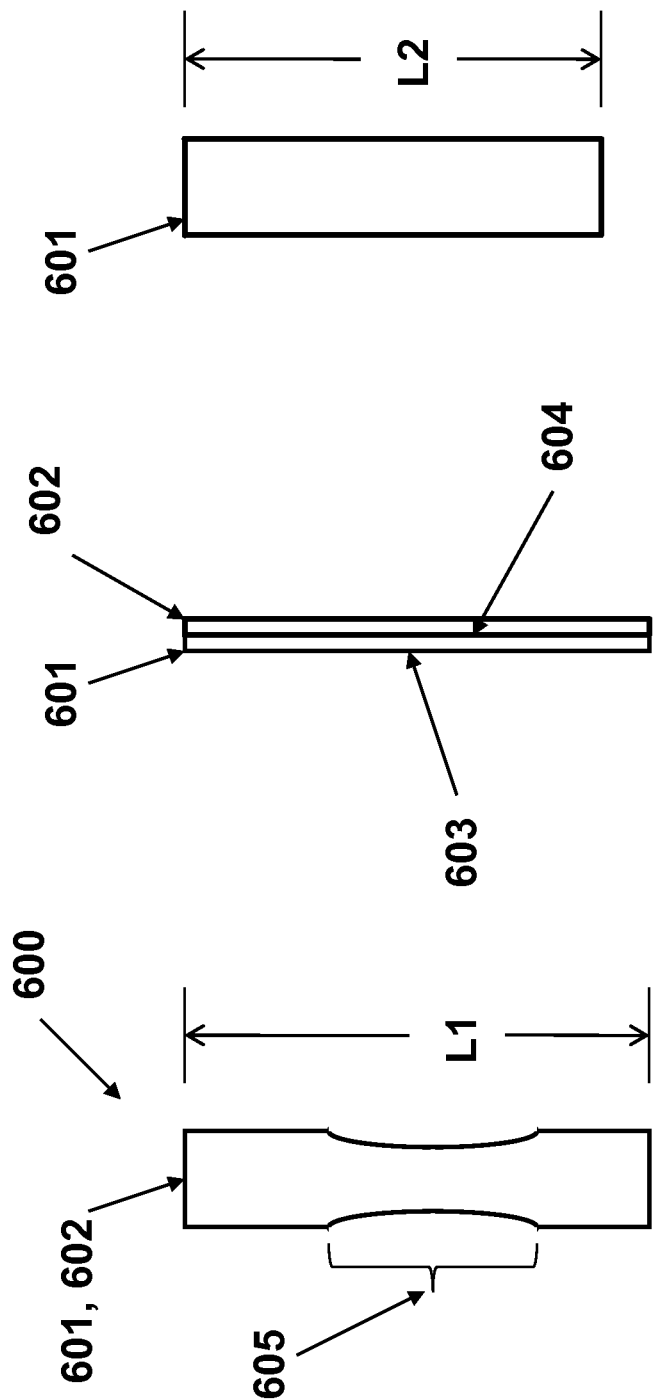

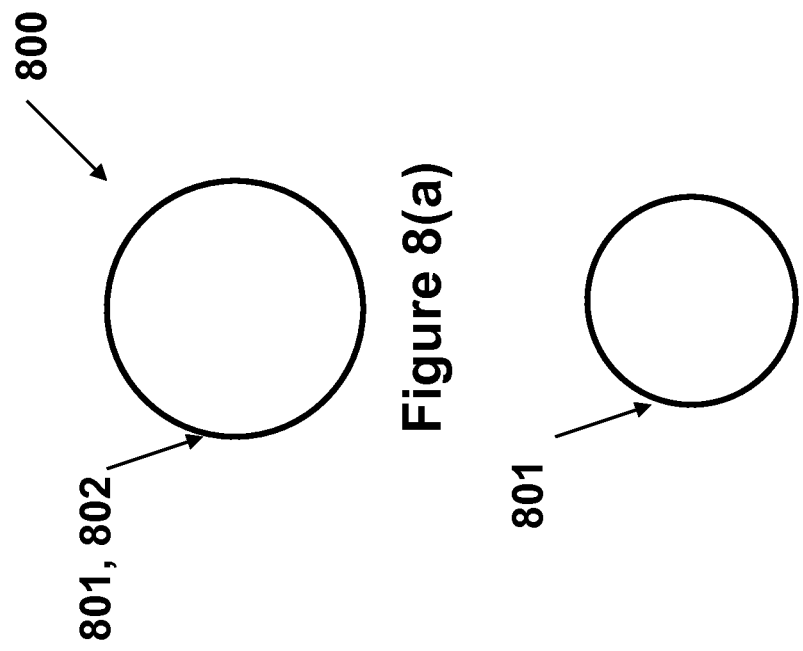
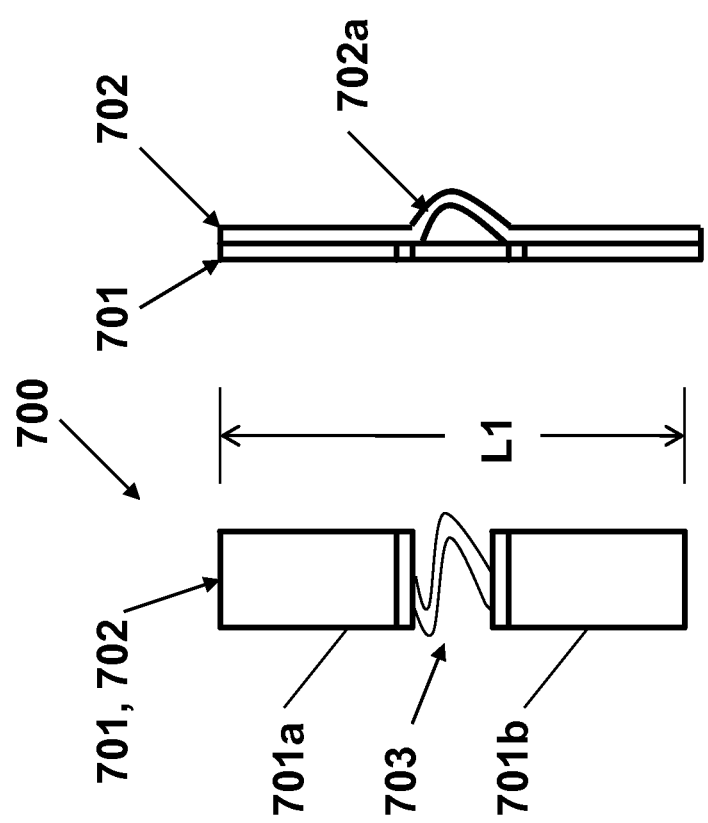

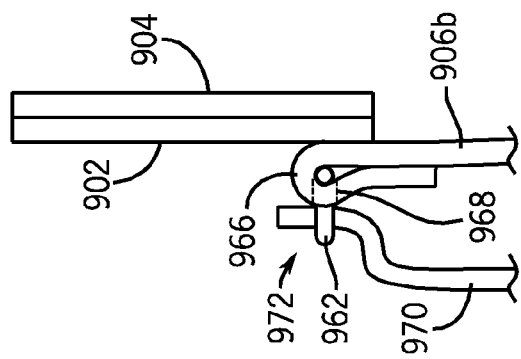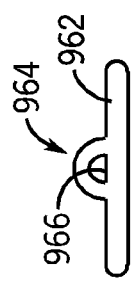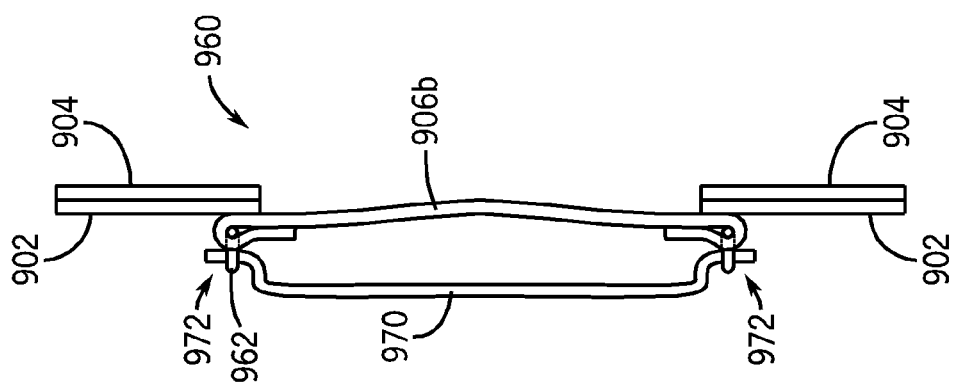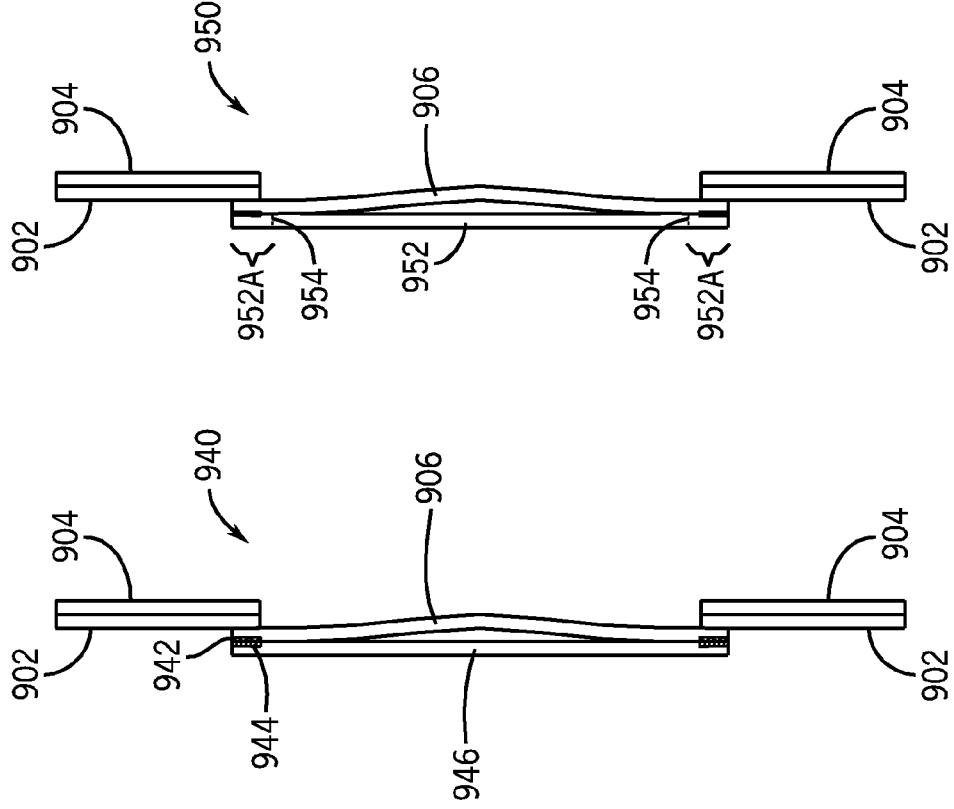

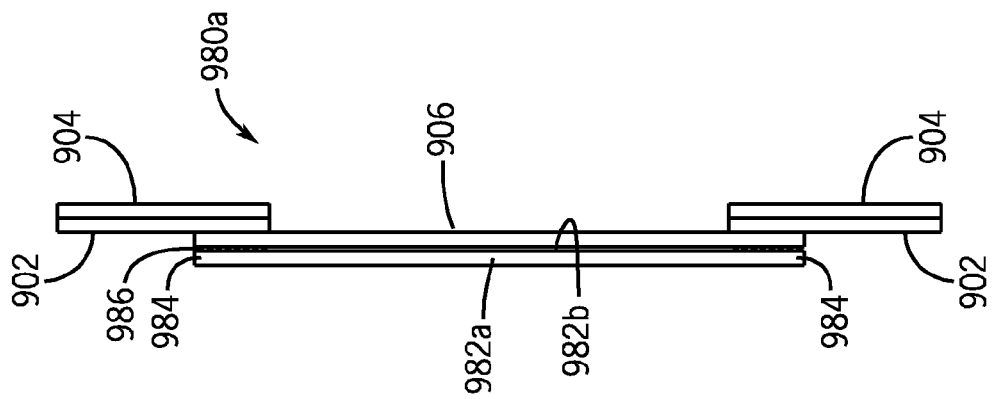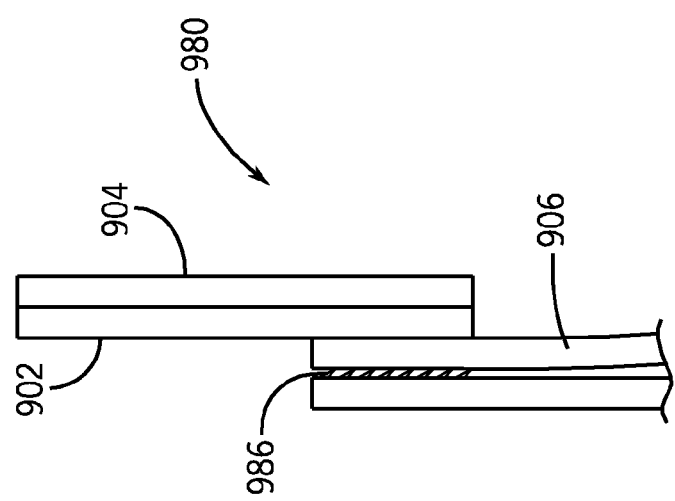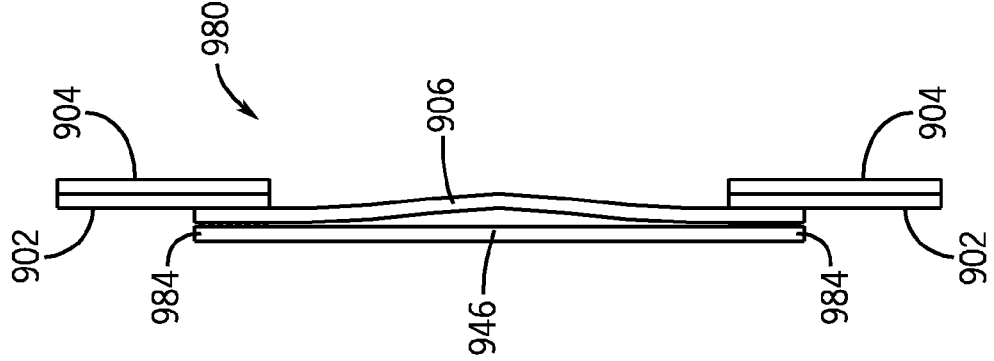

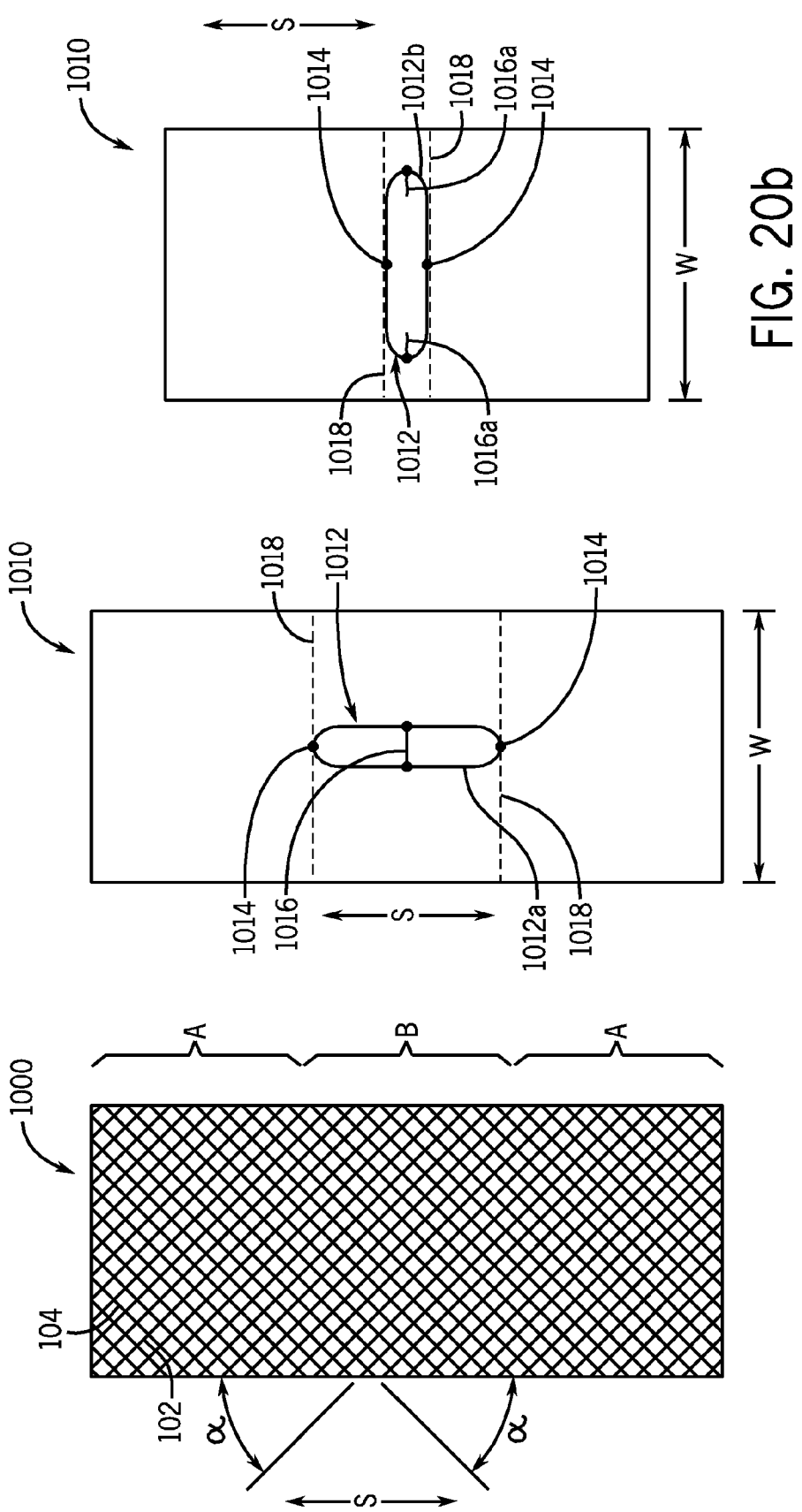

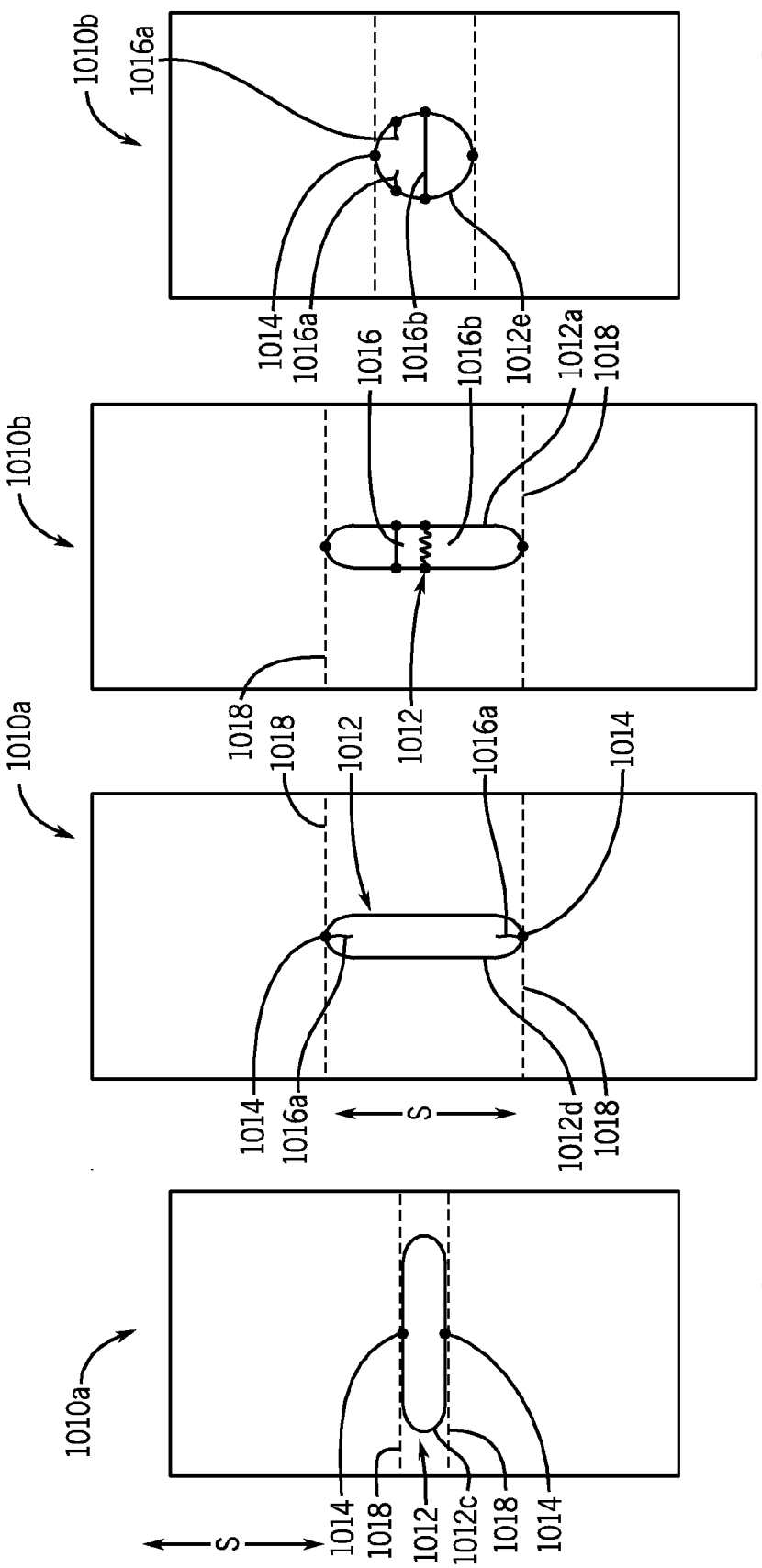

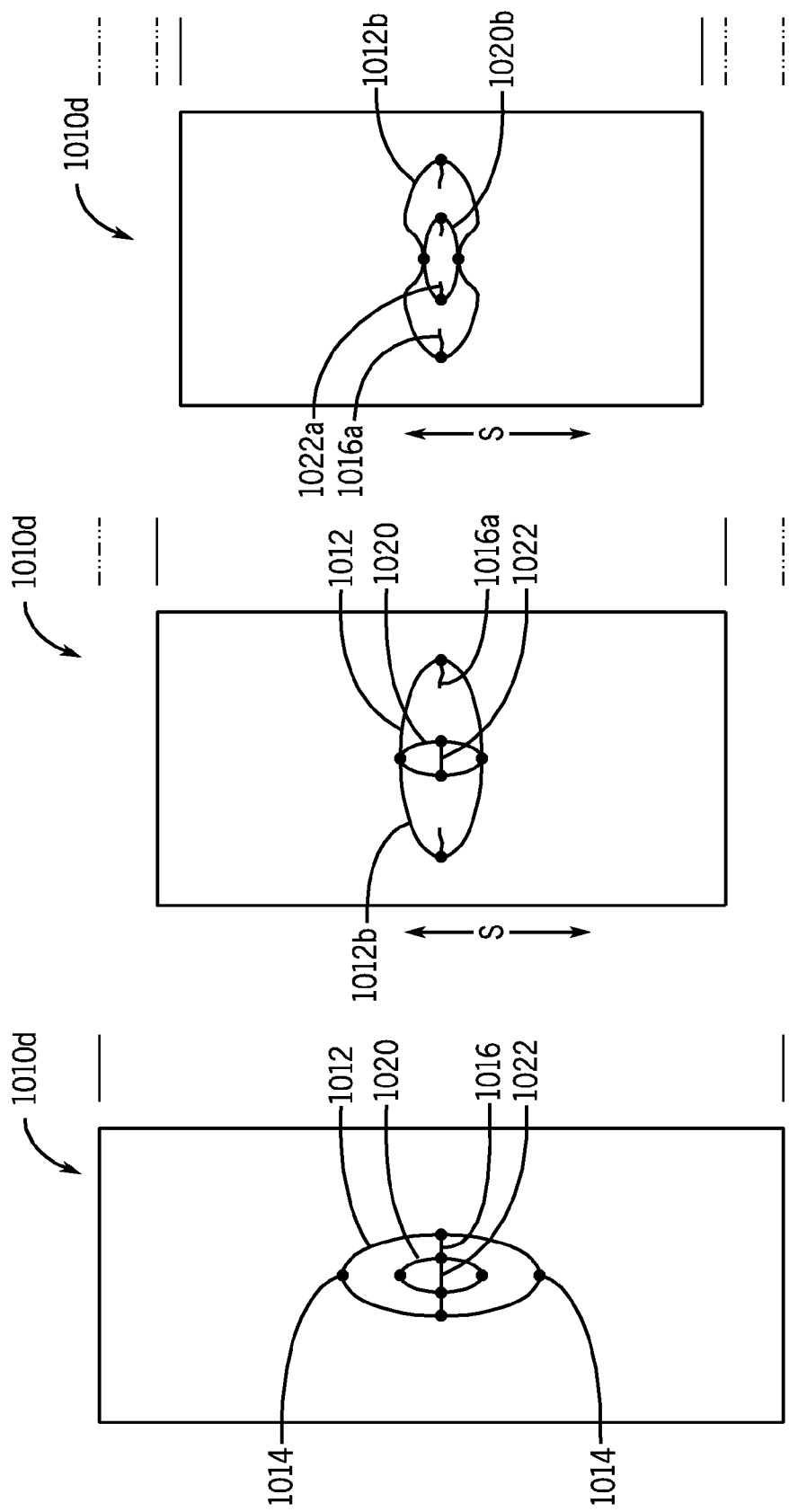

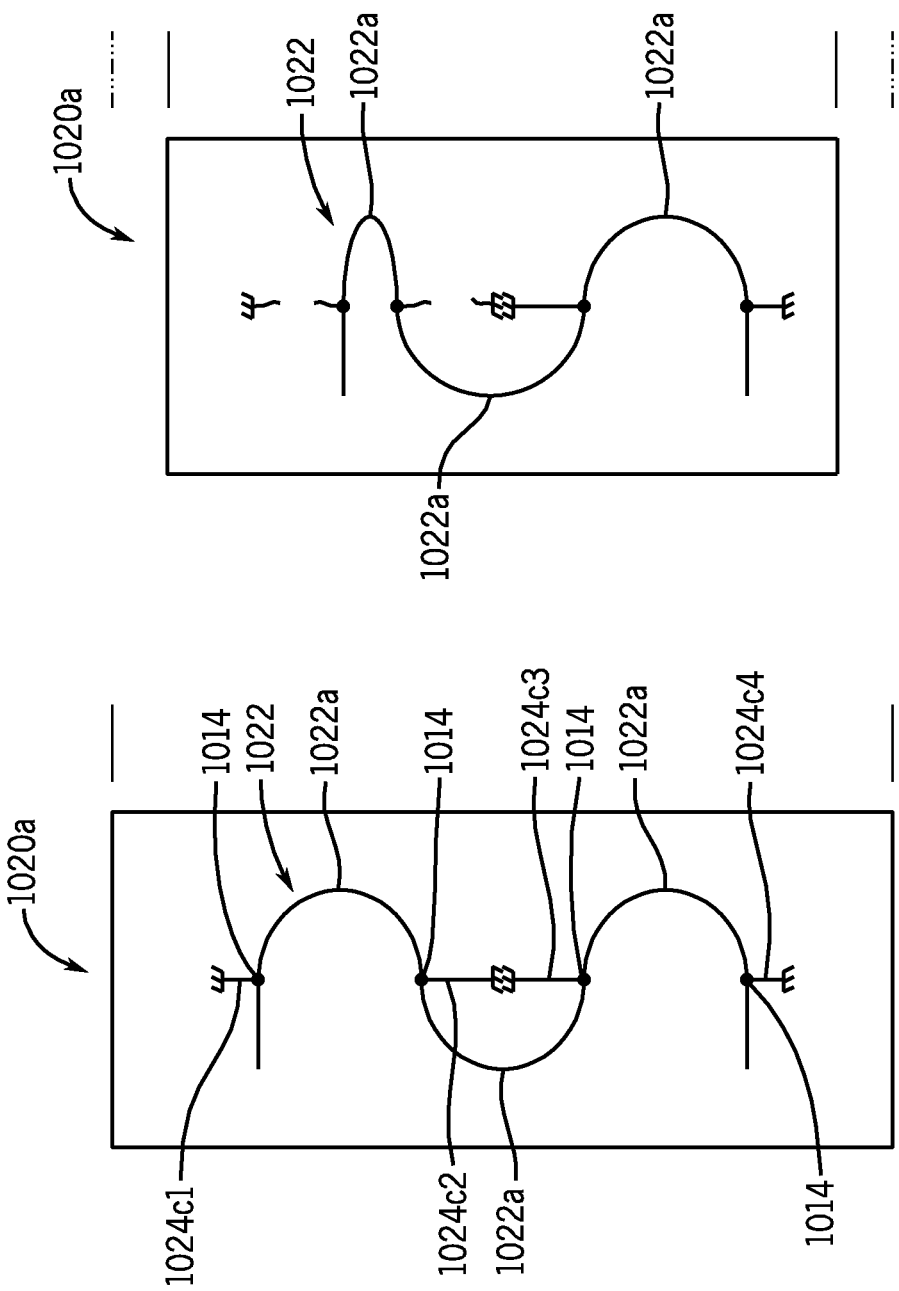

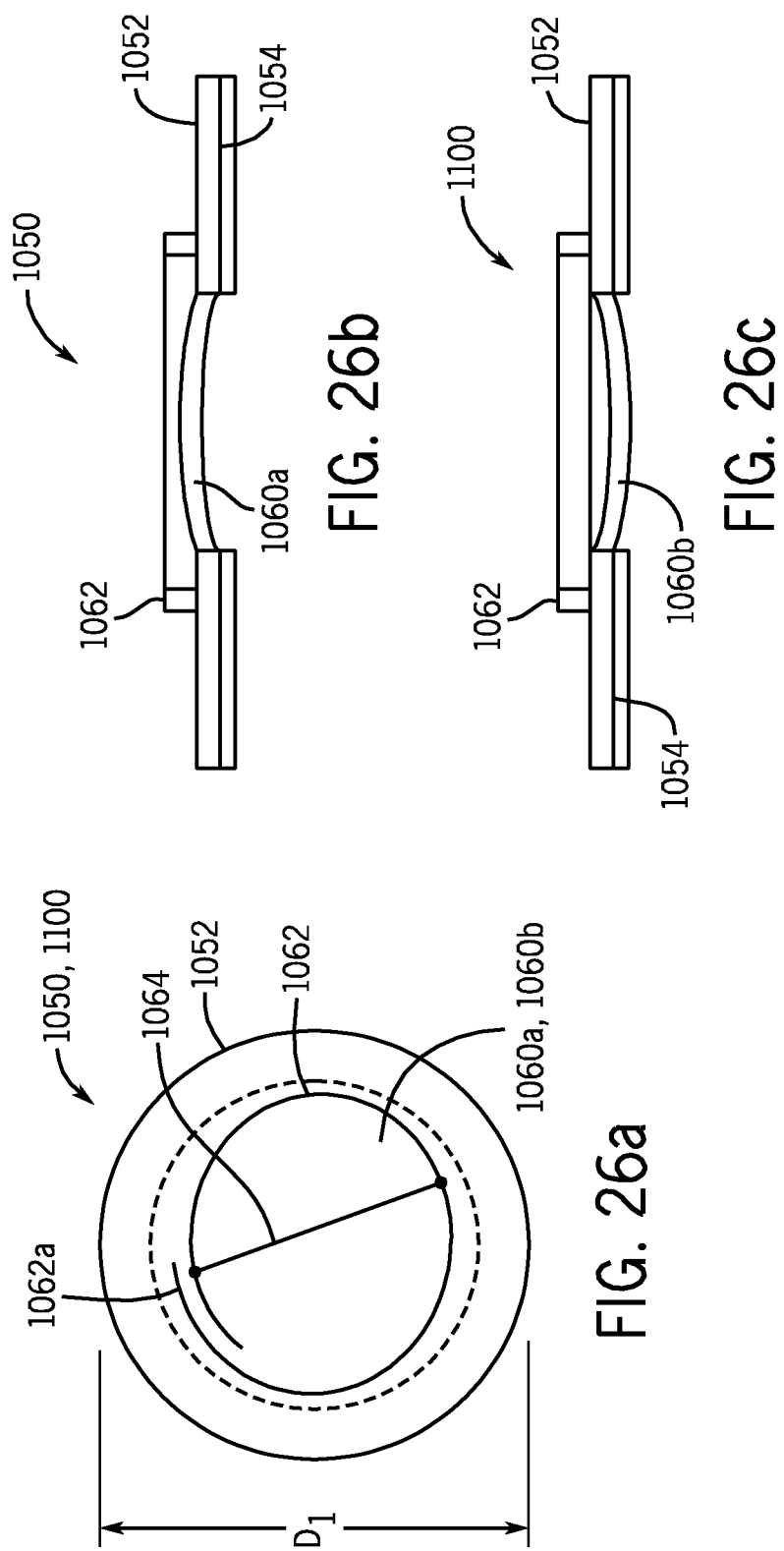

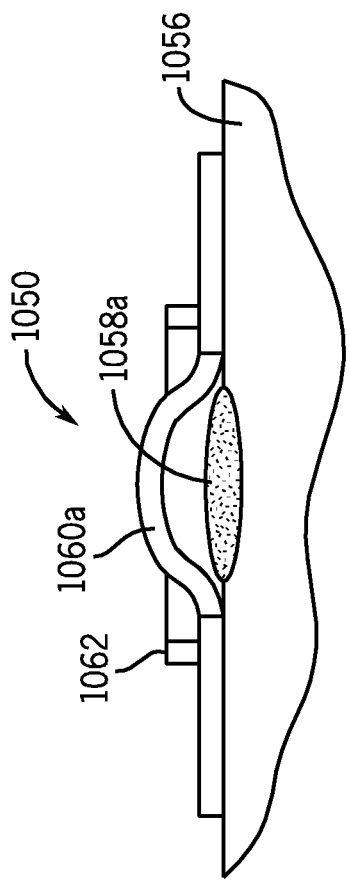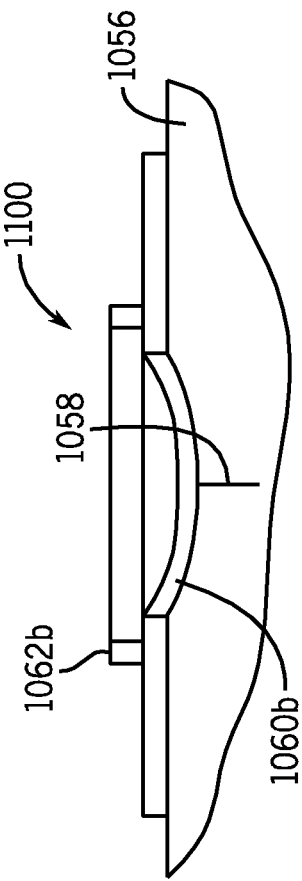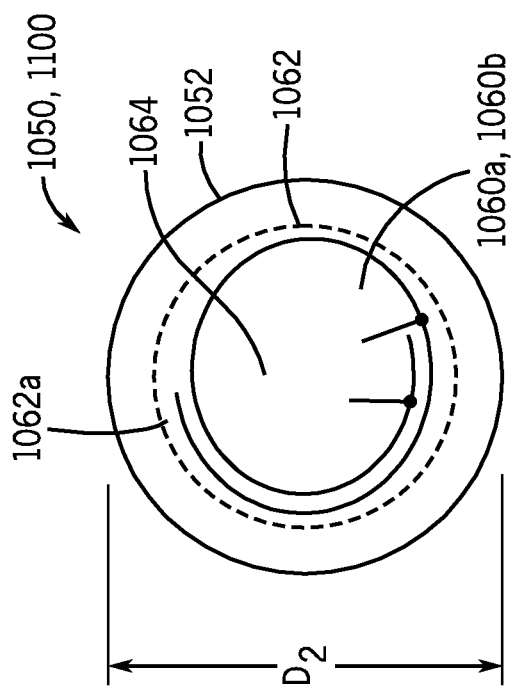

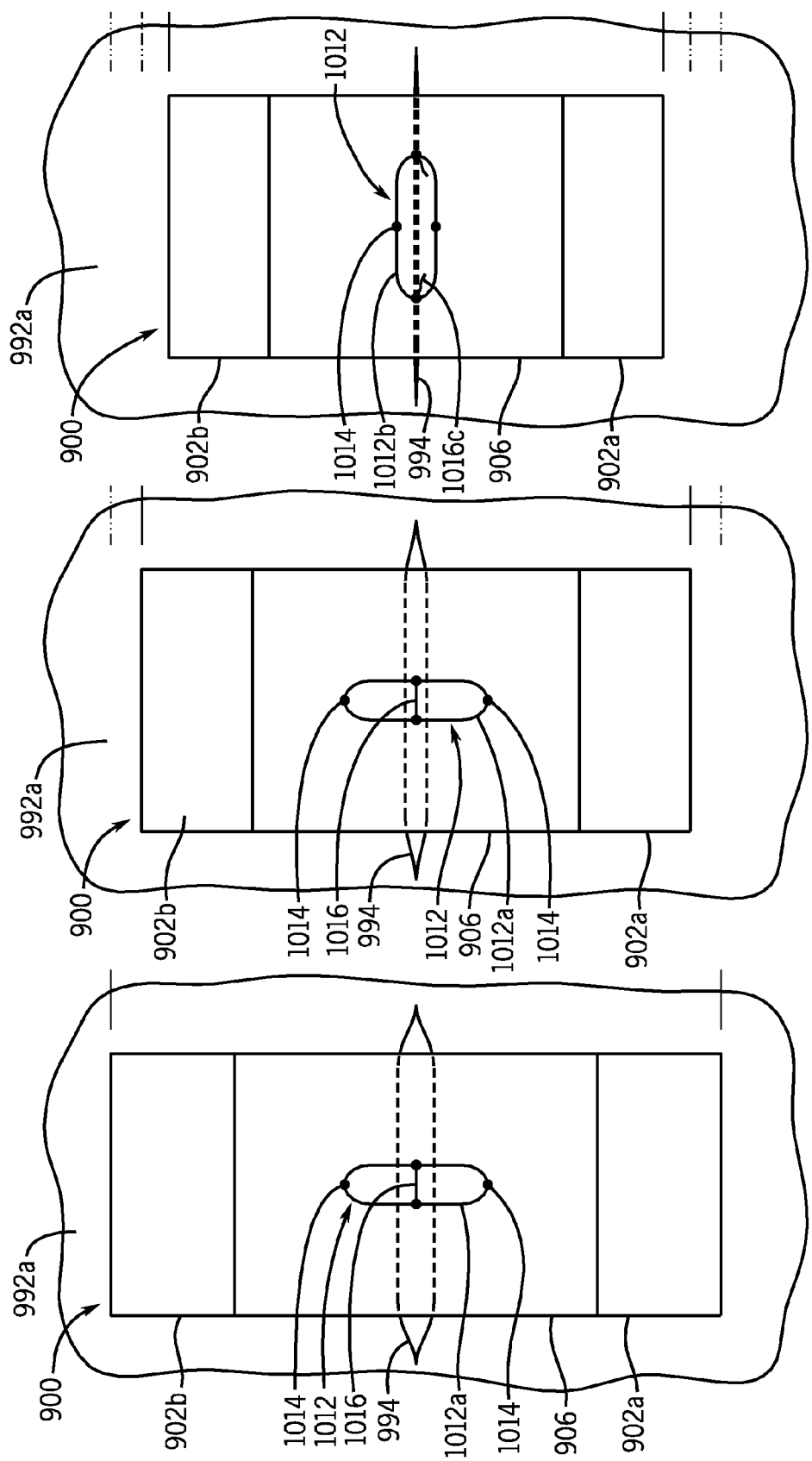

SHAPE AND PRESSURE ADJUSTABLE DRESSING

CROSS-REFERENCE TO RELATED APPLICATION

This application is a continuation-in-part application of U.S. application Ser. No. 13/046,767 filed on Mar. 13, 2011 which is a continuation-in-part application of U.S. application Ser. No. 12/983,314 filed on Jan. 2, 2011, the contents of which is incorporated herein by reference.

BACKGROUND

1. Field of the Invention

The present invention relates generally to dressings, and more specifically to shape and pressure adjustable dressings.

2. Prior Art

In many situations, dressings are desired to apply a certain amount of pressure on a wound or to apply a certain amount of force to close a wound or keep it closed, even over time as inflammation subsides. In other situations, it may be desired to increase the pressure or force over time to assist healing without a change in the dressing. In yet other situations it may be desirable to vary the pressure or force distribution over time. However, the currently available materials used for dressing wounds are difficult if not impossible to be used to achieve the above results in general, and to achieve it with ease and in a reliable manner in particular, even with the use of such aids as elastic components or tension fixtures.

In other situations, the dressing may be required to cover certain surfaces over the body that due to the shape of the surfaces, it may be difficult to make a close fit and even more difficult to apply pressure to the surface and sustain the applied pressure over time. In such situations, the dressing has to not only conform to the covered surfaces, but at the same time may have to provide a certain pattern of pressure or force to achieve certain goals.

A need therefore exists for a method to construct dressings that can be readily applied to the desired area, and then have the capability of its shape to be varied and/or apply a desired pattern of pressure or force to the covered area. The disclosed methods of varying the shape of the component just before use, is also advantageous in many applications since it can be used to reduce the size of the required packaging, e.g., a blister shaped component may be initially stored as a relatively flat sheet and then be turned to a blister just before application to the patient's skin.

SUMMARY

Accordingly, a dressing for application to skin is provided. The dressing comprising: a portion; an adhesive applied on a surface of the portion for adhering the portion to the skin; an elastic member associated with the portion and restrained into a first shape; and a restraining member connected to the elastic member to maintain the elastic member in the first shape; wherein when the restraining member is removed from restraining the elastic member, the elastic member moves towards an unrestrained second shape to one or more of elongate or reduce a dimension of the portion to apply a pressure to corresponding portions of the skin.

The portion can have a rectangular shape. The adhesive can be applied to the surface of the portion at first and second ends of the rectangular shape. The first and second ends can be separated in a lengthwise direction. The first and second ends can be separated in a widthwise direction.

The elastic member can have a circular shape. The adhesive can be applied to the surface of the portion at an annular ring of the circular shape.

The portion can be constructed of first and second portions, each having the adhesive applied on a surface of the first and second portion for adhering the first and second portions to the skin.

The portion can include portions for facilitating application of the portion to the skin in a non-linear shape. The portions can comprise a series of notches disposed at one or more of an edge of the portion.

The elastic member can be configured so as to reduce or enlarge the dimension in one or more of a width or length of the portion.

The elastic member can be configured so as to reduce the dimension in a diameter of the portion.

The elastic member can comprise two or more elastic members. The two or more elastic members can be arranged in one or more of a width direction or a length direction of the portion. At least one of the two or more elastic members can be arranged interiorly of another of the two or more elastic members.

The elastic member can have a closed, open or complex shape.

The elastic member can be attached to a surface of the portion.

The elastic member can be formed interiorly to the portion.

The elastic member can be at least partially formed integrally with the portion.

The restraining member can be a tensile member. The tensile member can be one or more of a flexible or rigid member.

The restraining member can be a rigid compressive member.

The restraining member can be connected to at least two points on the elastic member.

The restraining member can comprise two or more restraining members, each connected to the elastic member.

The two or more restraining members can be configured such that removal of each one incrementally moves the elastic element from the first shape towards the second shape through one or more intermediate shapes.

The two or more restraining members can have one or more of a differing length or elasticity.

The portion can include one or more rigid portions for facilitating the elongation or reduction in the dimension over a width of the portion. The one or more rigid portions can comprise a bar. The one or more rigid portions can comprise an embossed part of the portion.

The portion can have at least a part that is formed of an elastic material. The elastic material can be a woven fabric having one or more of weft and warp fibers being elastic.

The elastic member can have a second elastic member and the portion can be formed at least partially of a first elastic member restrained into a shape in which the portion is applied to the skin. The restraining member can restrain both the first and second elastic members.

Also provided is a method for applying pressure to skin with a dressing. The method comprising: adhering at least a portion of the dressing to the skin; and subsequent to the adhering, changing the shape of the dressing by removing a restraint which restrains an elastic member associated with the dressing into a first shape; wherein the removing of the restraint from restraining the elastic member moves the elastic member towards an unrestrained second shape to one or more of elongate or reduce a dimension of the dressing to apply a pressure to corresponding portions of the skin.

Further provided is a method for applying pressure to skin with a dressing. The method comprising adhering a first portion of the dressing to the skin; with the first portion adhered to the skin, changing the shape of the dressing from a second shape to a first shape by application of a force to the dressing to elastically deform the dressing; with the dressing in the second shape, applying a second portion of the dressing to the skin where the first and second portions bridge a wound on the skin such that an elastic force in the dressing tending to return the dressing to the second shape closes the wound; and subsequent to the applying of the second portion of the dressing to the skin, further changing the shape of the dressing to further close the wound by removing a restraint which restrains an elastic member associated with the dressing into a third shape; wherein the removing of the restraint from restraining the elastic member moves the elastic member towards an unrestrained fourth shape to further close the wound.

still yet also provided is a woven fabric comprising: having a body with a length longer than a width; and end portions of the body in a length direction having less elasticity than a central portion of the body between the end portions; wherein weft and warp fibers forming the body are arranged offset from the length direction and a width direction.

BRIEF DESCRIPTION OF THE DRAWINGS

These and other features, aspects, and advantages of the apparatus and methods of the present invention will become better understood with regard to the following description, appended claims, and accompanying drawings where:

FIG. 1(a) illustrates a first embodiment of a dressing having a first layer and a second layer.

FIG. 1(b) illustrates the dressing of FIG. 1(a) in which the first and second layers are separated.

FIG. 1(c) illustrates the first layer of FIG. 1(b) after the second layer has been separated therefrom.

FIG. 2(a) illustrates the dressing of FIG. 1(a) attached to the surface of skin.

FIG. 2(b) illustrates the dressing of FIG. 2(a) after the second layer has been removed.

FIG. 3(a) illustrates two component sheets of a second embodiment of a dressing.

FIG. 3(b) illustrates the two component sheets of FIG. 3(a) attached into an assembly.

FIG. 3(c) illustrates one of the components of FIG. 3(b) attached to the skin of a patient and the other of the components separated therefrom.

FIG. 5(a) illustrates a top view of yet another embodiment of a dressing.

FIG. 5(b) illustrates a side view of the dressing of FIG. 5(a) when at a temperature lower than a threshold temperature.

FIG. 5(c) illustrates the dressing of FIGS. 5(a) and 5(b) attached over a cut in skin.

FIG. 5(d) illustrates the dressing of FIG. 5(c) after the dressing has attained a temperature greater than the threshold temperature to close the cut in the skin.

FIG. 6(a) illustrates a top view of yet another embodiment of a dressing.

FIG. 6(b) illustrates a side view of the embodiment of FIG. 6(a).

FIG. 6(c) illustrates the dressing of FIGS. 6(a) and 6(b) after the second layer has been removed.

FIG. 7(a) illustrates a top view of a variation of the embodiment of FIG. 6(a).

FIG. 7(b) illustrates a side view of the embodiment of FIG. 7(a).

FIG. 8(a) illustrates a top view of another variation of the embodiment of FIG. 6(a).

FIG. 8(b) illustrates the dressing of FIG. 8(a) after the second layer has been removed.

FIG. 13 illustrates yet another embodiment of a dressing.

FIG. 14 illustrates yet another embodiment of a dressing.

FIG. 15A illustrates yet another embodiment of a dressing.

FIG. 15B illustrates a partial enlarged view of the dressing of FIG. 15A.

FIG. 15C illustrates a clip used in the dressing of FIG. 15A.

FIG. 16A illustrates yet another embodiment of a dressing.

FIG. 16B illustrates a partial enlarged view of the dressing of FIG. 16A.

FIG. 16C illustrates a variation of the embodiment of FIGS. 16A and 16B.

FIG. 19 illustrates an alternative woven portion for a dressing capable of deforming from the second shape into the first shape.

FIGS. 20a and 20b illustrate another alternative dressing portion.

FIGS. 20c and 20d illustrate an alternative of the dressing portion of FIGS. 20a and 20b.

FIGS. 20e and 20f illustrate another alternative of the dressing portion of FIGS. 20a and 20b.

FIGS. 22a-22c illustrate an alternative of the dressing portion of FIGS. 21a-21c.

FIGS. 24c and 24d illustrate an alternative dressing portion of FIGS. 25a and 25b.

FIGS. 26a-26f illustrate two additional embodiments of a dressing having utility for puncture wounds.

FIGS. 27a-27c illustrate a variation of the dressing of FIGS. 18a-18c.

DETAILED DESCRIPTION

Figure 4C:
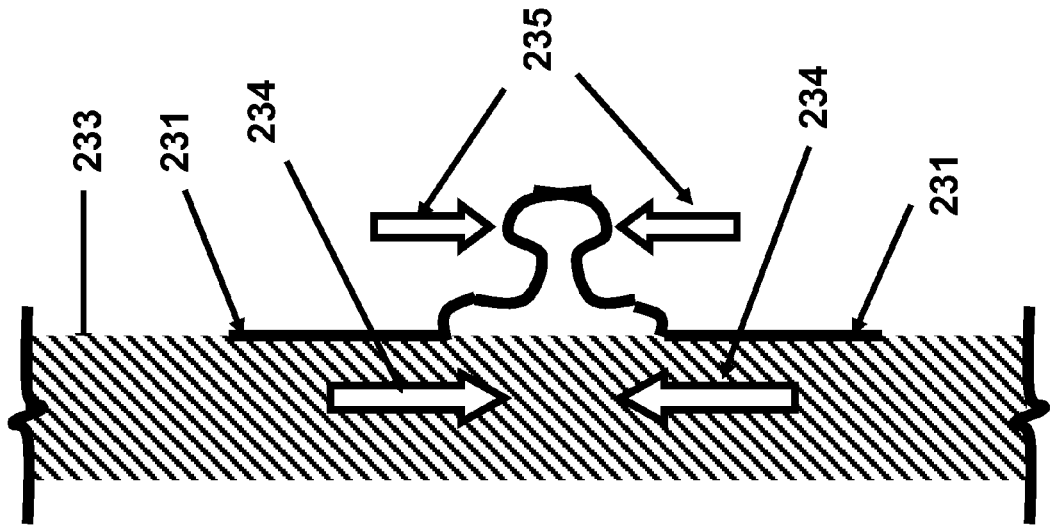
FIG. 4(c) illustrates the dressing of FIG. 4(b) being compressed together.

A schematic of a basic design based on a first embodiment is shown in the FIGS. 1(a) to 1(c). In FIG. 1(a), the cross-section of a plane assembly 100 is shown, and consists of a first layer 101 and a second layer 107. The two layers are attached together using any methods known in the art, such as with adhesives, so that the user could readily separate them. The layer 101 consists of components 102 and 104, which are attached together with an intermediate component 103. Similarly, the components 104 and 106 are attached together with an intermediate component 105. The components 102, 104 and 106 are considered to be relatively devoid of internal stresses, while the components 103 and 105 have been originally shaped as shown in FIG. 1(c), but have been elastically flattened and held in the flattened configuration by the component 107, as shown in FIG. 1a, to form the assembly 100. Obviously, if the component (layer) 107 is separated from the assembly 100, as shown in FIG. 1(b), the components 103 and 105 would return to their original shape, and the layer 100 will take the shape shown in FIG. 1(c).

The first layer 101 can be formed of any material which can be fabricated into a certain (original) shape and elastically deformed into another shape, such as a plastic or metal or combination thereof. Furthermore, plate 107 can be formed of any material rigid enough to prevent the first layer 101 from taking the original shape while attached to the first layer.

In the schematic of FIGS. 1(a)-1(c), the assembly 100 is shown to be in the shape of a flat plate. It is, however, appreciated by those skilled in the art, that the assembly may form a curved surface; more stressed (preloaded or elastically deformed) and essentially unstressed (preloaded or elastically deformed) components may be used in the assembly; and in their unstressed state, the stressed (preloaded or elastically deformed) component(s) may have been constructed to assume a variety of shapes (configurations), including complex shapes and curvatures. In general, upon the removal of the constraining component(s), the stressed (preloaded or elastically deformed) component(s) will tend to return to their unstressed (natural) state. It is appreciated that the stressed component(s), while tending to return to their unstressed (natural) state (shape or configuration), may still retain part of their induced internal stresses.

The dressing assembly 100 may be applied to the body surface 110, e.g., via an adhesive layer on the free surface of the layer 101 (not shown), as can be seen in FIG. 2(a). Once the assembly 100 is securely attached to the body surface, the layer 107 (wholly or partially) is removed. FIG. 2(b) shows the case in which the layer 107 is removed. At least part of the preloading stresses in the components 103 and 105 are then released. As a result, the layer 101 tends to its natural (stress-free) state. The components 102 and 106 are then pulled towards each other in the direction 112, and the underlying skin is pulled together. Thereby if a cut was present in the section of the skin 111 between the 102 and 106 components, the above action would tend to force it closed. The component 104 of the layer 107 is also pushed away from the skin.

In the schematics of FIGS. 1(a)-1(c), for the sake of simplicity, only two distinct layers are used and only one of the layers is provided with the preloaded components. However, more than one layer can be utilized, and layers with partially preloaded components may also be used to construct the dressing components. It is also possible to construct devices that are constructed with at least two layers of fully preloaded components. In addition, the final assembly (assembly 100) does not have to be flat, and may assume any appropriate shape and configuration as dictated with the particular application.

It should also be noted that in the schematics of FIGS. 1(a)-1(c), and in the remaining illustrations, only living joints are illustrated at discontinuities in the first layer 101. It is, however, appreciated that regular joints, such as pin joints and/or sliding joints, may also be used in the construction of the present devices.

Another embodiment of a dressing is shown schematically in FIGS. 3(a)-3(c). The dressing assembly 200 shown in FIG. 3(b), consists of at least two components (sheets) 201 and 202, which in their free (natural) form are curved as shown in FIG. 3(a). The dressing 200 is assembled by deforming the components 201 and 202 to their assembly configuration and attaching them together, preferably using adhesives, to achieve their final (assembled) configuration. In FIG. 3(a), and for the sake of simplicity, the two components 201 and 202 are shown to be deformed in a symmetrical manner, which upon bending in the directions 203 and 204, respectively, could be nearly flattened to their final shape in the assembly. In this particular case, since the two components 201 and 202 are considered to be identical and with symmetrical initial deformation, then upon their assembly after being flattened would assume a flat configuration. It is readily seen that by using two or more components with varying shape, and/or size, and/or materials, and/or initial (free or natural) configuration, one could construct infinite number of assemblies, which upon partial or full removal of one or more of the components, the desired final shape, size, configuration, and when appropriate applied force (moment or torque) to the attached member, could be achieved.

In certain assemblies, it may be necessary to use less strong adhesives for assembling certain components of the assembly for reasons such as ease of removal. In such cases, it may be necessary to provide mechanical locking action, such as by bending sides or corners of one component over the other, or by using attachment methods such as sewing or stapling or by using one or more clipping elements, etc., which is/are readily removable before applying the dressing to the patient or following its application. FIG. 3(c) illustrates the dressing 200 attached to a surface of the skin and sheet 202 removed, in which case sheet 201 is deformed towards its original shape and the skin takes the shape of the sheet 201 and is pulled together.

Figure 4B:
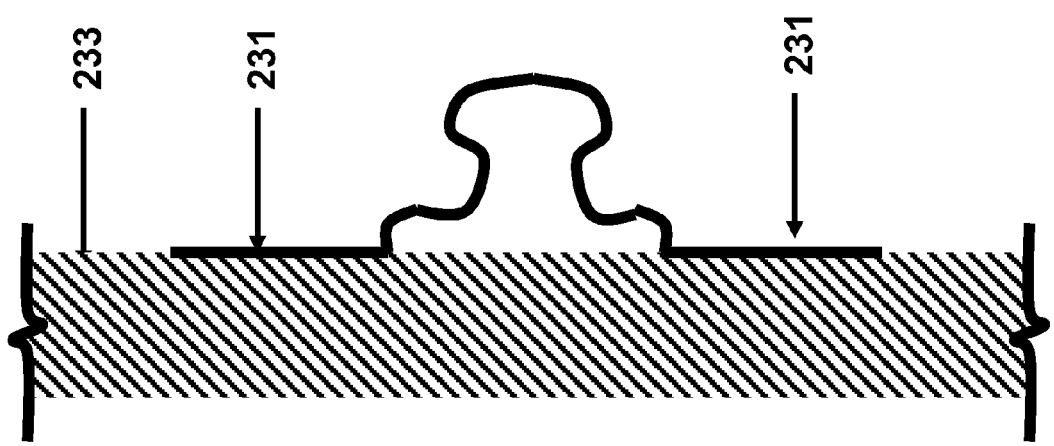
FIG. 4(b) illustrates the dressing of FIG. 4(a) attached to skin of a patient.
Figure 4A:
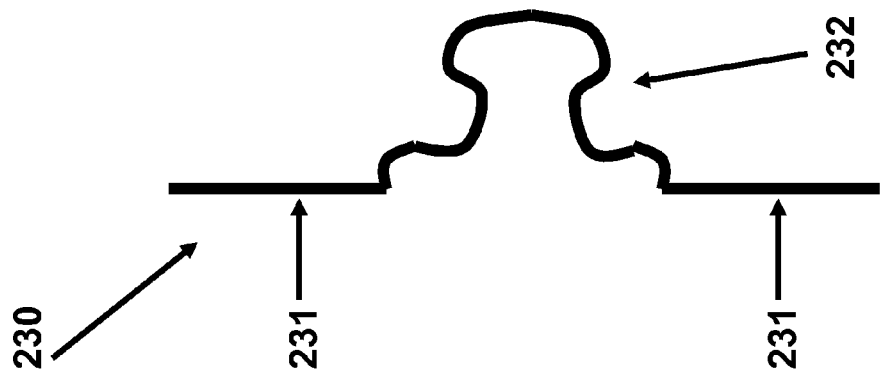
FIG. 4(a) illustrates another embodiment of a dressing.

Yet another embodiment of a dressing is shown in FIGS. 4(a)-4(c). The schematic of the side view of a plate formed with two flat sides 231 and a middle side 232, forming a simple example of a dressing element 230 is shown in FIG. 4(a). The adhesives that are preferably provided on these surfaces may then apply the dressing element 230 to the surface of the skin 233 as shown in FIG. 4(b), via the surfaces 231. The part 232 is then compressed together (or twisted or otherwise deformed) in the direction of bringing the surfaces 231 together (direction 235), such as with a tie-wrap, string wire or the like. As a result, the underlying skin is pulled together in the direction 234, thereby closing a wound or providing a desired compressive pressure, or in short the desired effect.

In all the disclosed embodiments, appropriate dressing components such as gauzes, medications, etc., may be disposed (preferably in the middle regions) of the dressing assemblies to cover the wound. Ventilation or drainage ports may also be provided when appropriate in these regions. Elastic or removable elements may also be provided over or around such regions for administering medication. In certain cases, it may also be desirable to construct one or more components of the assembly with transparent materials so that the affected region could be observed.

In addition, the applied pressure or wound closing action of the dressing element may be increased or decreased over time by removing, e.g., a larger piece of the shape/configuration affecting components or by further deformation of the shape/configuration affecting components. The pressure applied by the dressing can also be varied so that the skin can be "pushed" and "pulled."

Referring now to FIGS. 5(*a*)-5(*d*), the component 101, 201 disposed on the skin can be formed, at least in part, of a shape memory material. Thus, when disposed on the skin, the component 101, 201 can change shape, in whole or in part, due to a shape memory effect upon being heated by the temperature of the skin to at or above a transition temperature of the shape memory material. An external heat source may also be used to affect the shape change. Such materials are well known in the art and can be either metals or plastics which exhibit the shape memory effect. A dressing having such a configuration can eliminate the second component 107, 202 since the shape memory material can take one form, such as flat, at a first temperature (FIG. 5(*b*)) and take another shape, such as that shown in FIG. 5(*d*) at a second temperature. Thus, the plate 107, 202 is not needed to maintain the sheet 101, 201 in the shape shown in FIGS. 5(*a*) and 5(*b*). In this configuration, the dressing component can be shaped as shown in FIG. 5(*d*) when subjected to a temperature above the threshold temperature (e.g., body temperature) and can be flat when subjected to a temperature lower than the threshold temperature.

This dressing has particular utility when used as a butterfly type dressing for closing wounds that may otherwise require stitches. In this regard, the plan or top view shape of the dressing 101, 201 can be shaped like a conventional butterfly bandage having a narrowed section in the middle thereof, as shown in FIG. 5(*a*). Once placed over a cut 300 on the skin 302, such as with adhesive on a face 303 of the dressing 101, 201, as shown in FIG. 5(*c*), preferably disposed on the surface outside of the narrowed portion. After the dressing 101, 201 is warmed by the body heat of the skin, the shape memory material changes its shape to another shape, such as that shown in FIG. 5(*d*) to close the cut 300 by applying pressure in the direction of arrows 304. The portion of the dressing 101, 201 contacting the cut 300 may have a gauze and/or a medicated layer.

In a variation of such embodiment, the shape memory material dressing can be kept cool and applied to the skin while it is cold. Then the room temperature will activate it to change its shape so that you are not limited to activation with body temperature, which might be very close to the environmental temperature.

Other active materials that could be employed for the dressing could be active polymers, which would require a voltage to get them to pull.

Another embodiment will now be described in which the shape of the dressing changes after release of a release member, similar to those described with regard to FIGS. 1-4, where the shape change is a change in length of the dressing. FIG. 6(*a*) illustrates a dressing for a wound, generally referred to by reference numeral 600. The dressing 600 includes a first component 601, which can be a first layer, having a first shape with a first length L1. The dressing 600 further includes a second component, which can be a second layer, which is releasably attached to a first surface 604 of the first component 601 to maintain the first component 601 in a second shape different from the first shape. In the embodiment of FIGS. 6(*a*)-6(*c*), the second shape has a second length L2 which is longer than the first length. An adhesive is disposed on a surface 603 of the first component 601 different from the first surface 604 for attaching the first component 601 to the wound such that the second component 602 can be released from the first component 601 to allow the first component to take the first shape to apply a pressure to portions of the skin surrounding the wound to close the wound.

Thus, the dressing 600 is applied to the skin by adhering the surface 603 to the skin while the first component 601 is constrained into the first shape have a length L1. The second component 601 is then removed from the first component 601 to remove such constraint and allow the first component 601 to take the second shape having a shorter length L2, thus applying pressure to the skin which tends to close a wound.

The first component 601 can be formed of any material which can be fabricated into the first shape and elastically deformed into the second shape, such as an elastic material which can elastically stretch in at least one direction. Furthermore, the second component 602 can be formed of any material rigid enough to prevent the first component 601 from taking the second shape while attached to the first component 601.

In addition to an elastic material, the change of shape from the first length L1 to the second length L2 can be achieved by any other means for elastically biasing the first component 601 into the first length L1, such as one or more elastically deformed members attached at one end to a first portion of the first component and attached at a second (or another end) to a second portion of the first component. An example of such, referred to by reference numeral 700, is illustrated in FIGS. 7(*a*) and 7(*b*) having a biasing member 703 attaching first and second portions 701*a*, 701*b* of the first component 701. Such biasing member 703 can be of any material, such as plastic or metal that can elastically deform into the first shape and back to the second shape. FIG. 7(*b*) illustrates the second component 702 having a loop portion 702*a* adjacent to the biasing member 703 for facilitating removal of the second component.

The first component can have such elastic properties throughout the length L1 or a portion thereof, such as portion 605 which is adjacent to the wound. Also, although the embodiment of FIGS. 6(*a*)-6(*c*) is described with regard to a shape change in one direction, such shape change can occur in a different direction (such as perpendicular to the direction shown) or in more than one direction (such as in the direction shown and a direction perpendicular thereto). An example of such is shown in FIGS. 8(*a*) and 8(*b*), referred to by reference numeral 800, in which the first shape of the first component is a first diameter (shown in FIG. 8(*a*)) and the second shape is a second diameter smaller than the first diameter (shown in FIG. 8(b)). Such a variation is useful to apply pressure to the skin in more than one direction to close a wound, such as a puncture wound.

As discussed above, the first component can further include one or more of a medicament and gauze. As also discussed above, the two components can be attached together using any methods known in the art, such as with adhesives, so that the user could readily separate them and more intermediate components (not shown) can be used.

Figure 9B:
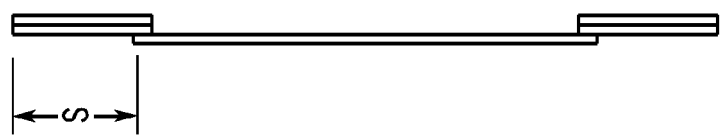
FIGS. 9A and 9B illustrate a side view of the dressing of FIG. 9 in a first shape and second shape, respectively, where the second shape is elongated.
Figure 9A:
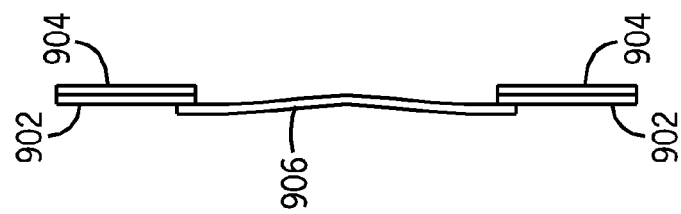

Another embodiment of a shape and/or pressing adjustable dressing will now be described with regard to FIGS. 9, 9A and 9B, referred to generally with reference numeral 900. The dressing 900 includes adhesive portions 902 at each end of the dressing 900 having an adhesive for adhering to skin and a release layer 904 which is releasably adhered to the adhesive portions such that it can be removed when the adhesive portions are to be adhered to the skin. The dressing further includes a portion 906 capable of being elastically deformed from a first shape to a second shape. As discussed above, the change in shape can take a great number of forms, such as being elongated, as shown in FIG. 9B (stretched by "S"). In the case where portion 906 changes shape by elongating, the same can facilitate such elongation with biasing elements or elastic material. The adhesive portions 902 and portions 906 can be connected together by sewing, adhering, heat welding and the like. Further, although the adhesive portions 902 and portion 906 are illustrated as separate portions, the same can be integrally formed. As will be described below, the dressing 906, and variations thereof, can be used to close a wound by itself (see FIGS. 18A-18C) or with various holding members, examples of which are described below (see FIGS. 10A-16B). The holding member has been referred to alternatively above as a second component and the adhesive portions 902 and portions 906 as a first component.

Figure 10B:
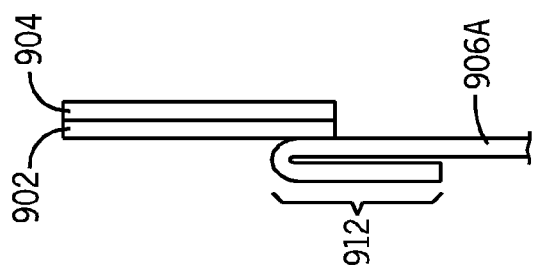
FIG. 10B illustrates a partial section view as taken along line 10B-10B in FIG. 10A.
Figure 10A:
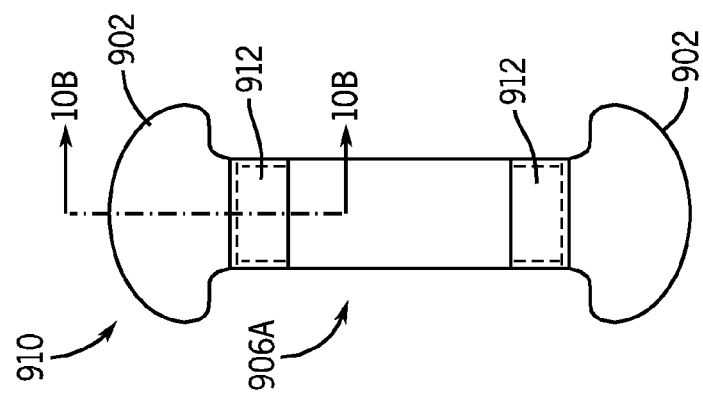
FIG. 10A illustrates a top view of yet another embodiment of a dressing.
Figure 9:
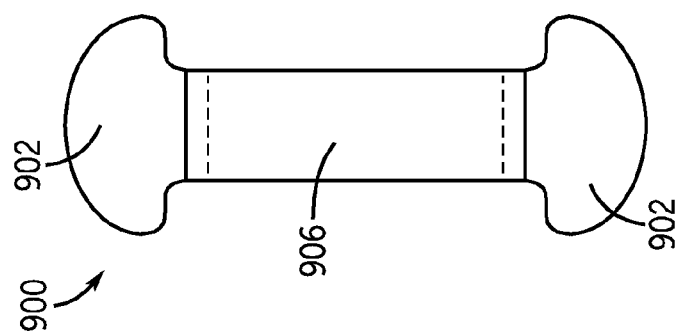
FIG. 9 illustrates a top view of yet another embodiment of a dressing

FIGS. 10A and 10B illustrate a first variation of the dressing 900 of FIG. 9 in which the dressing is used together with a holding member. The dressing, generally referred to by reference numeral 910, is similar to that of the dressing in FIG. 9 in which like reference numerals refer to similar features, except that a pocket 912 is formed at each of two ends of the portion 906A. The pocket 912, as shown in FIG. 10B can be formed by folding over an end of the portion 906A on itself and closing the same to form a pocket 912, by sewing, adhering, heat welding or the like.

Figure 10D:
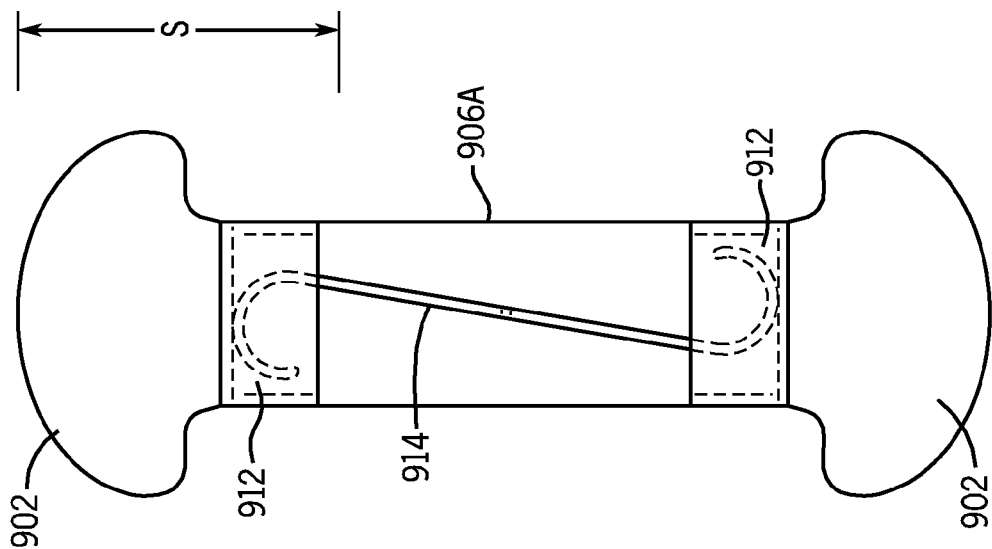
FIG. 10D illustrates a top view of the dressing of FIG. 10A held in an elongated shape with the holding member of FIG. 10C.
Figure 10C:
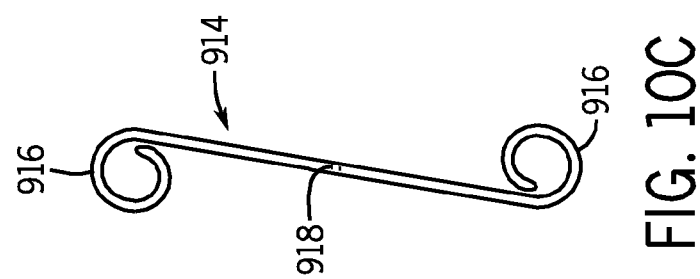
FIG. 10C illustrates a holding member for use in the dressing of FIG. 10A.

FIG. 10C illustrates a holding member 914 which can take any number of shapes, such as having curved ends 916 and a weakened portion 918. The length of the holding member is such that when the curved ends 916 are disposed in the pockets 912, the portion 906A changes shape by elongating a distance "S". The holding member 914 can be formed of many materials, such as wire, plastic and the like as long as it is rigid enough to maintain the portion 906A in the elongated state and may also be flexible such that the holding member and dressing can be applied over a curved surface of the skin. Although shown elongated flat, the holding member can also maintain the portion 906A elongated in a non-linear shape, such as curved.

As discussed above, the dressing 910 can be applied to the skin in the elongated state by removing the release layers 904 and adhering the dressing to the skin about the wound. After application to the skin, the holding member 914 can be removed or released such that the portion 906A can return to or towards its first shape. Such can be achieved by simply removing the holding member 914 from the pockets 912 or cutting or breaking the holding member 914, such as with a weakened portion 918. Such weakened portions are well known in the art and can include a perforated area or reduced cross-section area.

Figure 11:
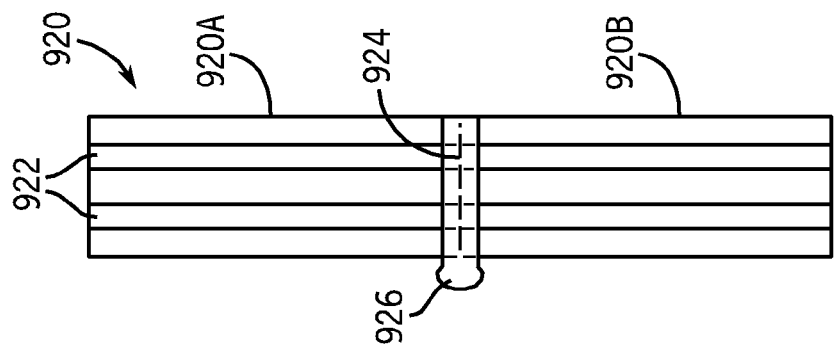
FIG. 11 illustrates an alternative holding member for use with the dressing of FIG. 10A.

As shown in FIG. 11, the holding member can also be a thin member 920 which can have one or more ribs 922 for added rigidity. The thin member can be formed of any material such as plastic. The thin member 920 can be simply removed from the pockets 912 or cut or broken, such as with a weakened portion 924. The weakened portion 924 can be as described above, and may also be realized by forming the thin member of two pieces 920A, 920B and holding the same together with tape 926 or other retaining means. When the dressing is desired to change to or towards its first shape (e.g., un-elongated), the tape is simply removed and the two resulting pieces 920A, 920B of the holding member 920 can be easily removed.

Figure 12:
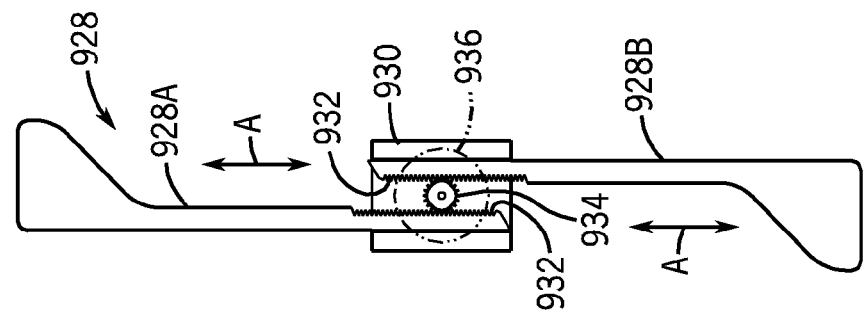
FIG. 12 illustrates another alternative holding member for use with the dressing of FIG. 10A.

FIG. 12 illustrates another example of a holding member 928, in which the length thereof is variable, so as to provide a user of the dressing with a desired elongation depending on the severity of the wound and/or other factors. The holding member 928 includes first and second portions 928A and 928B which are movable relative to each other. For example, the holding member 928 can include a sleeve 930 in which the first and second portions 928A and 928B can move in the direction of arrow A. The first and second portions 928A and 928B can have teeth on an end thereof which mate with a gear 934 which is rotatable on the sleeve 930. Rotation of the gear 934 results in the first and second portions 928A and 928B moving in the direction of arrow A. A knob 936 (shown in dashed lines) can be attached to the gear 930 to facilitate rotation of the gear 930. Thus, with holding member 928, the same dressing and holding member can be used to achieve different amounts of elongation for wounds of different severity.

FIG. 13 illustrates another dressing 940, in which one part of a hook and loop fastener 942 is attached to at least a portion of the adhesive portion 902 or portion 906 and the other part of the hook and loop fastener 944 is attached to at least a portion of a holding member 946. As discussed above, the holding member can be formed of a variety of materials such that it is rigid enough to maintain the portion 906 in the second shape (e.g., elongated) and may or may not be flexible to permit curvature of the dressing 940. When the dressing is desired to change to or towards its first shape (e.g., un-elongated), the hook and loop fastener bond is simply broken by removing the holding member 940.

FIG. 14 illustrates another dressing 950, in which each end portion 952A of a holding member 952 is adhered to a portion of the adhesive portion 902 or portion 906. Such adhesive bond can be removable or permanent. Where the bond is removable, the dressing is changed to or towards its first shape (e.g., un-elongated) by breaking the adhesive bond, i.e., by pulling the holding member 950 away from the portion to which it is adhered. Where the bond is permanent, the holding member can be cut or broken, such as at one or more weakened portions 954.

Referring now to FIGS. 15A, 15B and 15C, there is shown another embodiment of a dressing, referred to by reference numeral 960. The dressing 960 includes a clip 962 having a protrusion 964 with an opening 964. The clip 962 is retained in the portion 906b, such as with a loop 966 of material having an opening 968 for allowing the protrusion to extend from the portion 906b. The clip can be formed of plastic or metal or any material rigid enough for its intended purpose. A holding member 970 is used to maintain the portion 906b in a second shape, such as the portion 906b being elastic and the holding member 970 holding the portion 906b in an elongated state. The holding member 970 has ends 972, such as hooks, for engaging the opening 966 in the protrusion 964 of the clip 962. As discussed above, the dressing 960 is adhered to the skin about the wound by removing the release layers 904 and adhering the adhesive portions 902 to the skin. When the dressing 960 is desired to change to or towards its first shape (e.g., un-elongated), the holding member 970 is removed. Alternatively, the holding member 970 can be destroyed, such as by being cut or breaking the same about one or more weakened portions, as described above.

Referring now to FIGS. 16A and 16B, there is shown yet another embodiment of a dressing, referred to generally by reference numeral 980. The dressing 980 includes a holding member 982 having a surface 984 at each end thereof made of individual barbs 984. The barbs 984 at each can be angled away from each other so as to grab the portion 906 (and/or adhesive portions 904) and maintain the portion 906 in a second shape, such as in an elongated state. The holding member 982 can be formed of a material with sufficient rigidity to maintain the portion 906 in the second (e.g., elongated) shape, such as metal or plastic. After the dressing 980 is adhered to the skin about the wound by removing the release layers 904 and adhering the adhesive portions 902 to the skin, the holding member 982 is removed such that the dressing 960 can change to or towards its first shape (e.g., un-elongated). Alternatively, the holding member 980 can be destroyed, such as by being cut or breaking the same about one or more weakened portions, as described above.

Referring now to FIG. 16C, there is shown a variation of the dressing embodiment of FIGS. 16A and 16B, referred to generally by reference numeral 980a and in which like features are denoted with like reference numerals. In the dressing 980a of FIG. 16C, the holding member 982a has the surface 984 at each end thereof made of individual barbs 984. The barbs 984 at each can be angled away from each other so as to grab the portion 906 (and/or adhesive portions 904) and maintain the portion 906 in a second shape, such as in an elongated state. In addition, an adhesive, connects at least part of the surface 982b between the portion 906 and holding member 982a to further maintain the portion 906 in the second shape.

Figure 17A:
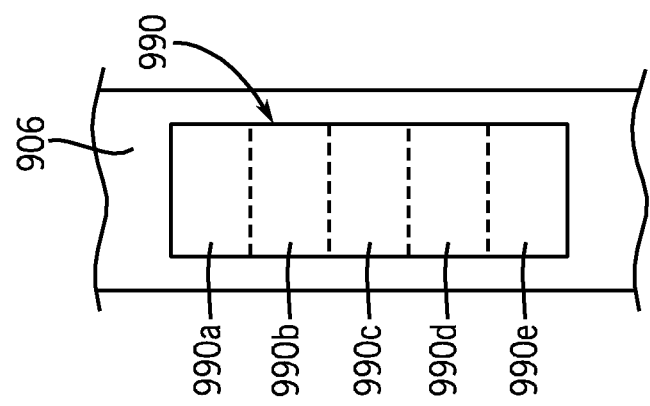
FIGS. 17A and 17B illustrate a variation of a dressing.
Figure 17B:
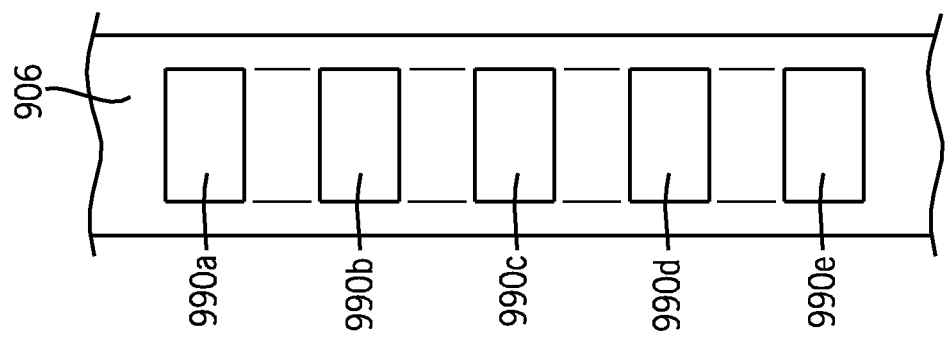

Referring now to FIGS. 17A and 17B, there is shown a variation for use with any of the embodiments described herein in which the portion 906 (906a, 906b) changes shape by being elongated. In such variation, the portion 906 includes a gauze pad 990 on a side thereof that contacts the wound. The gauze pad 990 includes strips 990a-990e. Although shown as 5 strips, the gauze pad 990 can be formed of two or more of such strips 990a-990e. The strips 990a-990e are positioned such that they form a continuous (or near continuous) gauze pad 990 when the portion is in its first un-elongated shape. That is, the strips 990a-990e accommodate the elongation of the portion 906 and separate when the portion 906 is elongated.

Figure 18A:
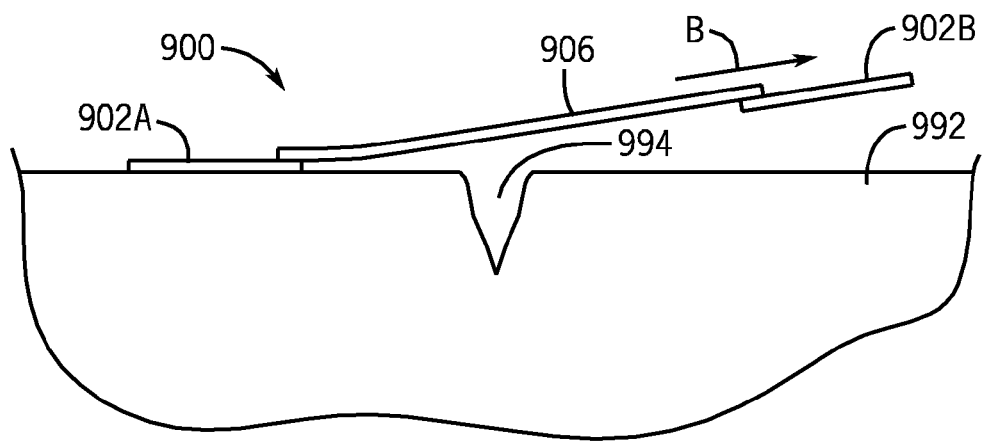
FIGS. 18A-18C illustrate a use of another alternative dressing.
Figure 18B:
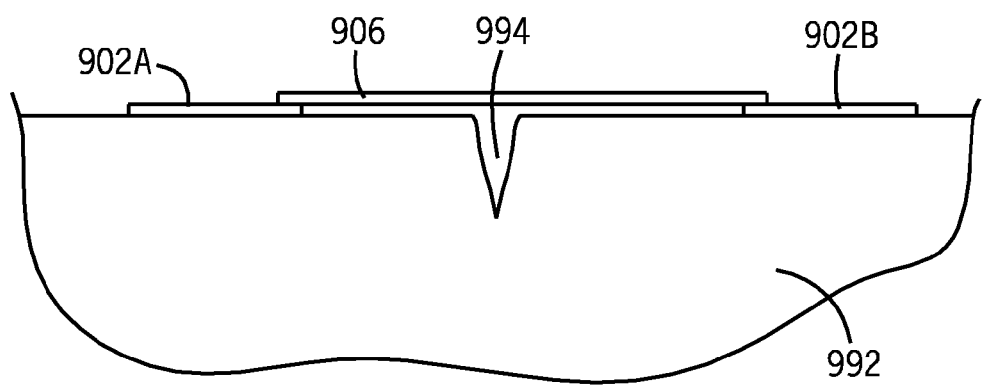
Figure 18C:
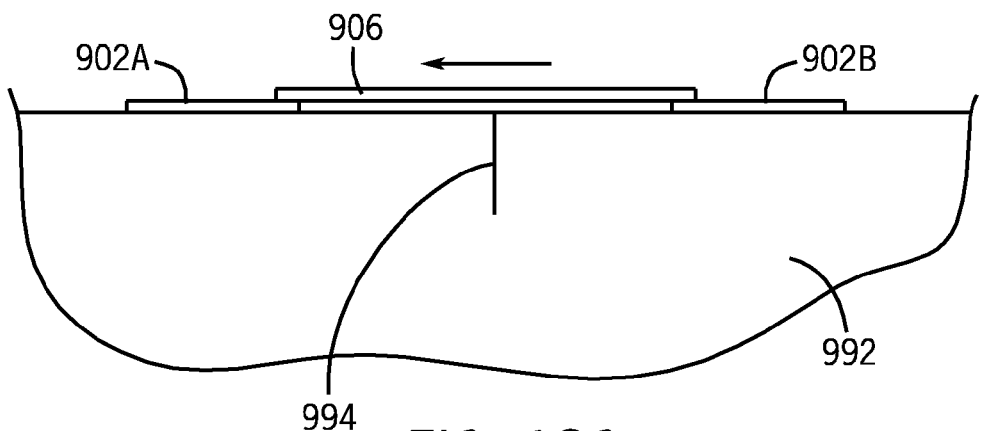

Referring now to FIGS. 18A-18C, the same illustrate an alternative use for the dressings illustrated above. Although applicable to the embodiments described above, the alternative use will be described by way of example with reference to the dressing of FIGS. 9, 9A and 9B. The alternative use for the dressing 900 does not make use of a holding member for maintaining the portion in a second (elongated) shape. As shown in FIG. 18A, one of the release members 904 is removed, exposing the adhesive on the adhesive portion 902A. The adhesive portion 902A is adhered to the skin 992 about a wound 994 to be closed/covered. With the release layer 904 from the other end removed, the dressing is urged into/towards its second shape, such as by pulling in the direction of arrow B and the other adhesive portion 902B is adhered to the skin 992 bridging the wound 994, as shown in FIG. 18B. The dressing 900 then tends to try to return to its first (un-elongated) shape resulting in the wound closing, as shown in FIG. 18C.

Thus, the alternative use described in FIGS. 18A-18C results in the wound closing with time, which, depending on the elastic force in the portion 906 and the severity of the wound, can be from a relatively short time to an extended time. The time delay results in less trauma to the patient because pulling the wound closed tightly at once can be painful. Furthermore, the portion can apply a constant pressure over time even though other variables change, such as a reduction in swelling. In dressings of the prior art, the dressing is pulled taught and applied to close the wound. However, such can be very painful to the patient and may not fully close the wound once swelling subsides.

The elastic force generated in the elastic portions described above can be due to a material that can be elastically deformed, such that it can be deformed into the second shape and be capable of elastically re-taking the first shape. An example of such a material is a woven material having at least one of a weft and warp fibers being elastic (e.g., formed of an elastomer, such as rubber) in the direction to be deformed (e.g., across the wound). Alternatively, at least one of the weft and warp fibers can be elastic in at least a component of the direction to be deformed.

Referring now to FIG. 19, the same illustrates an alternative portion 1000 for use in the embodiments discussed above in which the portion deforms from the second shape into the first shape. The portion 1000 is a woven fabric in which the weft and warp fibers 1002, 1004 are woven at an angle α offset from a stretching direction S, such as at 45°. Such a weaving pattern permits a central part B of the portion 1000 to have at least one of the weft and warp fibers 1002, 1004 to be elastic and other portions A to be at least partially formed such that the weft and/or warp fibers are non-elastic or less elastic than those used in part B. In this way, the central portion B of the portion 1000 can be elastic (e.g., elastically deform by stretching) and the other portions A be non-elastic (or less elastic). Thus, an adhesive for adhering the portion 1000 to the skin can be located on the other portions A and the stretchable portion B is disposed across the wound. This enables better adhesion of the portion 1000 to the skin and more effectively utilizes the elasticity of the portion 1000 and costs associated therewith by concentrating the elasticity only in the central portion that is associated with the wound. The adhesive for adhering portions of the portion 1000 to the skin, release members and holding member(s), if necessary, are not shown in FIG. 19 for the sake of simplicity.

Referring now to FIGS. 20a and 20b, the same illustrate a portion 1010 for use in the embodiments discussed above in which the portion deforms from the second shape (deformed, such as by being elongated) into the first shape (such as by being reduced in length and/or width). Such portion 1010 and others to follow can have integral or separate portions (e.g., 902) for adhering to the skin, as discussed above. If separate, such combination is still referred to hereinafter as a portion.

The portion 1010 can be formed of an elastic material that is at least capable of stretching in a direction S across a wound. The portion includes an elastic member 1012 formed thereon, such as by being adhered, embossed, attached by stitching, stapling, clipping or the like. The elastic member 1012 can be formed of materials capable of being elastically deformed, such as spring steel, plastic and the like. If stitched, the stitching 1014 can be at the points indicated by reference numeral 1014. The elastic member 1012 has a unrestrained shape 1012*b*, such as that shown in FIG. 20*b*, and is capable of being elastically deformed into a restrained (preloaded) shape 1012*a*, such as that shown in FIG. 20*a*. A restraining member, such as a tensile member, such as a string 1016, restrains the elastic member in the restrained shape 1012*a*. The restraining member 1016 can also be a rigid member. The restraining member can have a portion (not shown) to be grasped to facilitate pulling, cutting or breaking of the restraining member, such as a tab or knob. Thus, after adhering at least a part of the portion 1010 to the skin (or separately provided portions, such as portions 902 indicated above), as discussed above, with the elastic member 1012 corresponding to an area where a wound is located, the restraining member 1016 can be removed, such as by cutting or otherwise severing such that the elastic member 1012 can take the unrestrained shape 1012*b* (or at least try to take such shape by moving from the restrained shape 1012*a* towards the unrestrained shape 1012*b*) (the cut ends of the restraining member illustrated in FIG. 20*b* by reference numerals 1016*a*). As the elastic member 1012 moves from the restrained shape 1012*a* towards the unrestrained shape 1012*b*, the portion 1010 is reduced in length in the direction S. Rigid or semi-rigid bars 1018 (shown in broken lines) can be provided to facilitate the shape change along the width W (or portion thereof) of the portion 1010. The bars 1018 can be adhered or otherwise attached a surface of the portion 1010 or formed therein. Alternatively, the bars 1018 can be a more rigid portion of the portion 1010, such as by more densely formed weave or an embossing of the portion 1010.

FIGS. 20*c* and 20*d* illustrate a variation of the portion 1010 illustrated in FIGS. 20*a* and 20*b*. The portion illustrated in FIGS. 20*c* and 20*d* being referred to by reference numeral 1010*a* and having like reference numerals indicate like features. In the portion 1010*a*, the elastic member 1012 is arranged such that cutting or otherwise severing the restraining member 1016 while in the restrained shape 1012*c* results in the elastic member 1012 taking the unrestrained shape 1012*d* to elongate the portion 1010*a* in the direction S.

Different shape, size, configuration and material elastic members 1012 can produce different desired changes in length (reduction or enlargement) depending on the desired effect.

FIGS. 20*e* and 20*f* illustrate another variation of the portion 1010 illustrated in FIGS. 20*a* and 20*b*. The portion illustrated in FIGS. 20*e* and 20*f* being referred to by reference numeral 1010*b* and having like reference numerals indicate like features. The portion 1010*b* includes two restraining members, such as strings 1016 and 1016*b*. String 1016*b* being longer or having additional elasticity than string 1016. Thus, the change in shape in the direction S can be accomplished in a stepwise manner by providing two (or more) restraining members. That is, cutting or otherwise severing restraining member 1016 permits the elastic member 1012 to take an intermediate shape 1012*e* between the restrained shape 1012*a* and unrestrained shape 1012*b* because restraining member 1016*b* is longer or more elastic than retraining member 1016. Once restraining member 1016*b* is cut or otherwise severed, the elastic member can move towards the unstrained shape 1012*b* shown in FIG. 20*b*. More than two restraining members can be provided to produce more than one intermediate shape of the elastic member.

Figure 21C:
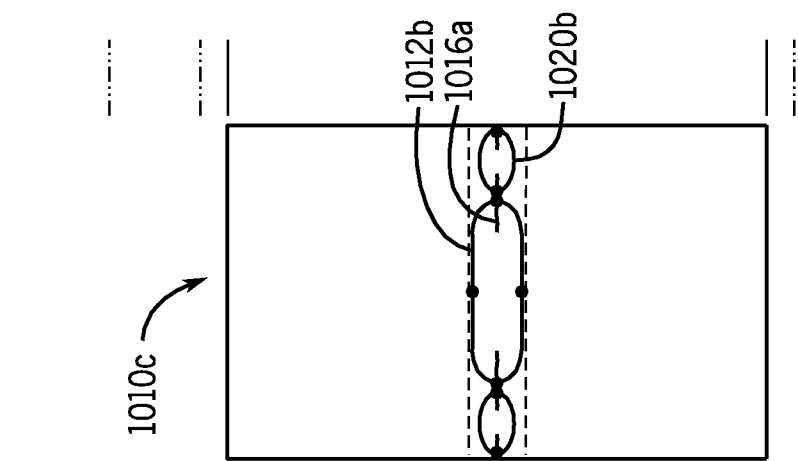
FIGS. 21a-21c illustrate another alternative of the dressing portion of FIGS. 20a and 20b.
Figure 21B:
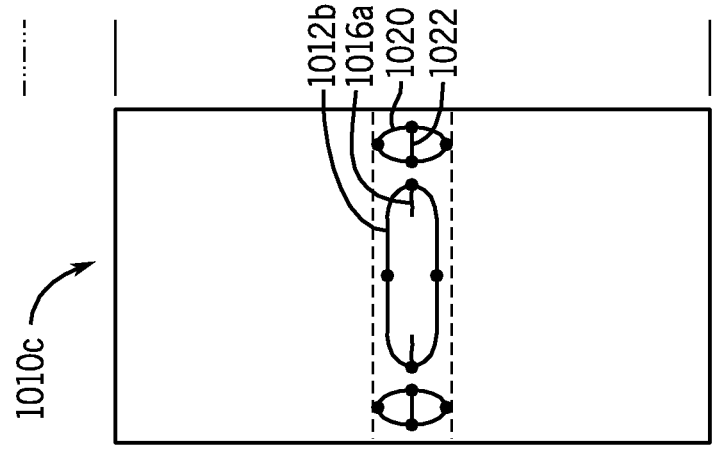
Figure 21A:
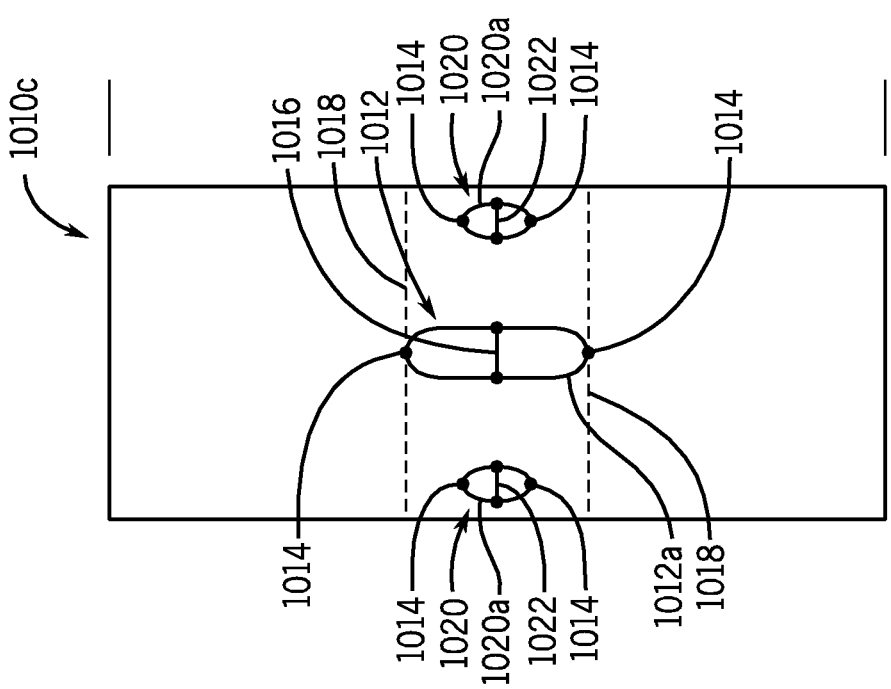

FIGS. 21*a*-21*c* illustrate another variation of the portion 1010 illustrated in FIGS. 20*a* and 20*b*. The portion illustrated in FIGS. 21*a* and 21*b* being referred to by reference numeral 1010*c* and having like reference numerals indicate like features. The portion 1010*c* illustrated in FIGS. 21*a* and 21*b* is also configured to change shape in the direction S in a stepwise manner by providing two (or more) elastic members. The first elastic member 1012 is configured as shown and described in FIGS. 20*a* and 20*b* and additional elastic members, such as 1020, are also provided and configured similarly such that they are in a restrained shape 1020*a* and move towards an unrestrained shape 1020*b*, shown in FIG. 21*c*. As shown in FIG. 21*b*, if the restraining member 1016 is cut or otherwise severed, the portion changes shape in the direction S, similarly to that shown and described with regard to FIG. 20*b*. Additionally, one or more of the restraining members 1022 can be cut or otherwise severed to produce an additional change in shape, as shown in FIG. 21*c*.

Alternatively, the plurality of elastic members (e.g., 1012, 1016) can be provided in the stretching direction S (similar to that shown in FIG. 25*a* but configured for a reduction in the length of the portion) so as to stepwise and selectively reduce the length of the portion 1010*c* in the stretching direction S. Such elastic members 1012, 1022 can be provided in the same sizes, different sizes, and configured for lengthwise and/or widthwise enlargement and/or reduction and/or components thereof.

FIGS. 22*a*-22*c* illustrate a variation of the portion 1010*c* illustrated in FIGS. 21*a*-21*c*. The portion illustrated in FIGS. 22*a*-22*c* being referred to by reference numeral 1010*d* and having like reference numerals indicate like features. The portion 1010*d* illustrated in FIGS. 22*a*-22*c* is configured to change shape in the direction S in a stepwise manner by providing two (or more) elastic members, similarly to that of portion 1010*c*. As in the portion 1010*c*, the first elastic member 1016 is configured as shown and described in FIGS. 20*a* and 20*b* and one or more additional elastic members, such as 1020 is also provided and configured similarly such that they are in a restrained shape 1020*a* and move towards an unrestrained shape 1020*b*, shown in FIG. 21*c*. However, the additional elastic members 1020 are provided within the shape of the first elastic member 1016. As shown in FIG. 22*b*, if the restraining member 1016 is cut or otherwise severed, the portion 1010*d* changes shape in the direction S, leaving the shape of additional elastic member 1020 unchanged (or changed but still capable of further change) similarly to that shown and described with regard to FIG. 20*b*. Additionally, the restraining member 1022 can be cut or otherwise severed to produce an additional change in shape, as shown in FIG. 22*c*. Although the bars 1018 are not shown in FIGS. 22*a*-22*c*, they can be provided for the benefits discussed above.

Figure 23:
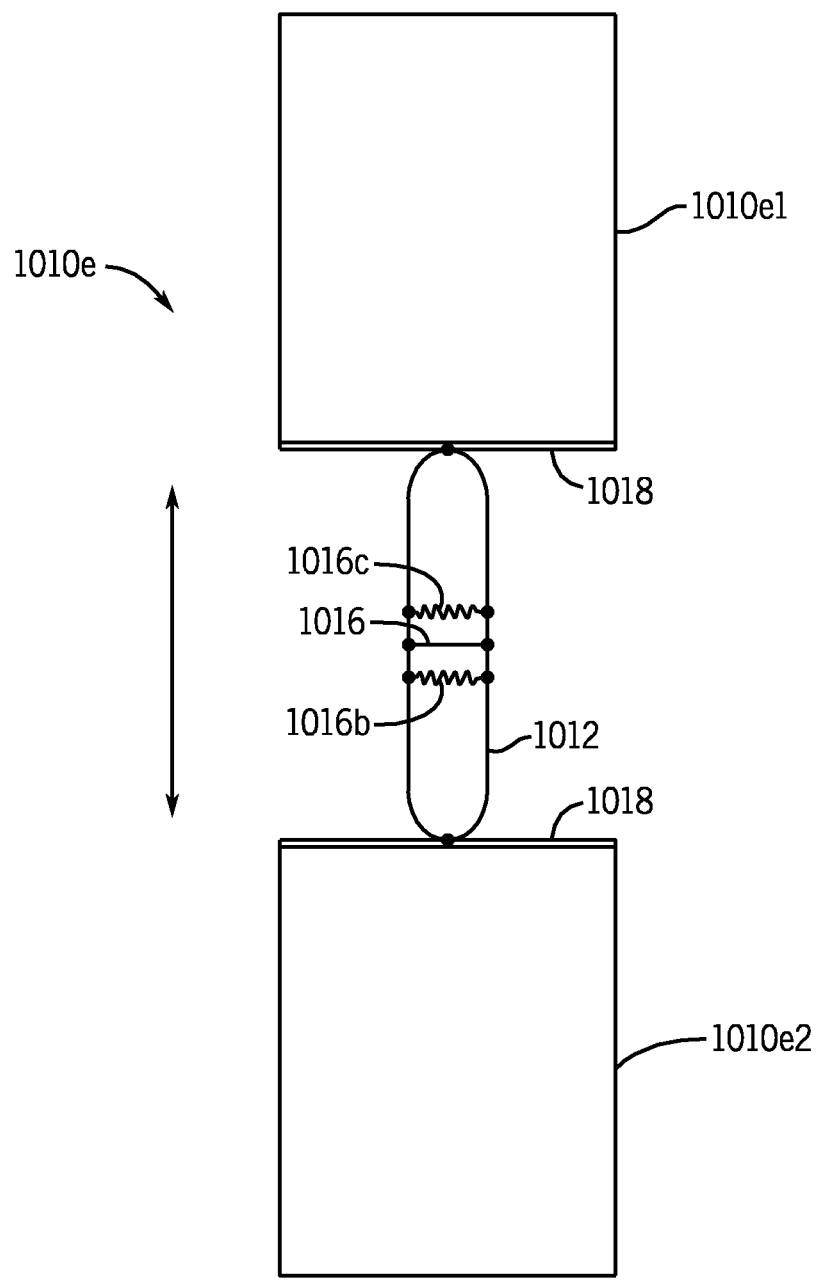
FIG. 23 illustrates an embodiment of a dressing portion.

Although the elastic members discussed above are shown attached to the portion and such portion changes shape (either stretches or shrinks along direction S) with the change in shape of the elastic member, such elastic member(s) as described above can be provided between first and second parts of the portion. Such a configuration is shown in FIG. 23. FIG. 23 illustrates a portion 1010*e* having first 1010*e*1 and second 1010*e*2 parts. Such parts 1010*e*1 and 1010*e*2 are connected by one or more elastic members 1012. Restraining members 1016, 1016*b* and 1016*c* having different lengths or degrees of elasticity can be provided to stepwise change the length of the portion in the direction S.

The portion 1010*e* can be used without a dressing to cover the wound or a conventional dressing can be applied over the wound.

Although not shown, a single elastic member having a complex shape (more than one curved and/or linear segments) can be provided with more than one restraining member, such that cutting each restraining member incrementally changes the complex shape to incrementally change the shape of the portion across the wound, such as in the direction S. Thus, the stepwise change in shape in the direction S can be accomplished with a single elastic member and more than one restraining member arranged between various points on the complex shape.

Figure 24C:
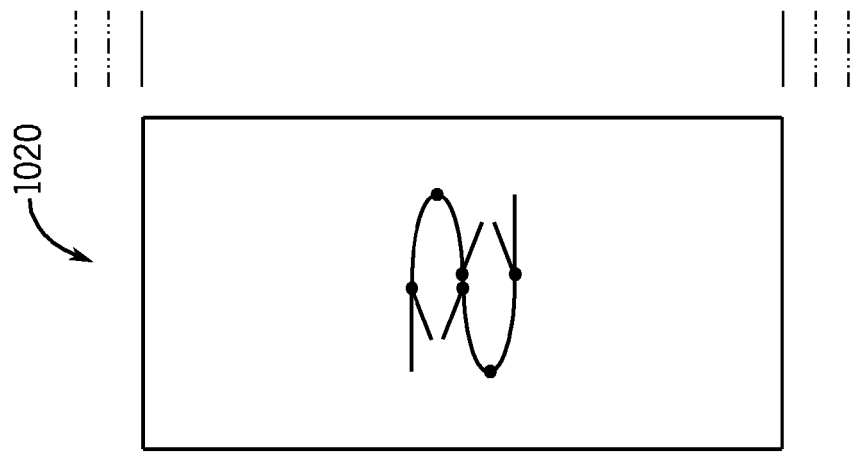
FIGS. 24a-24c illustrate another alternative dressing portion in which an elastic member having a complex shape is provided.
Figure 24B:
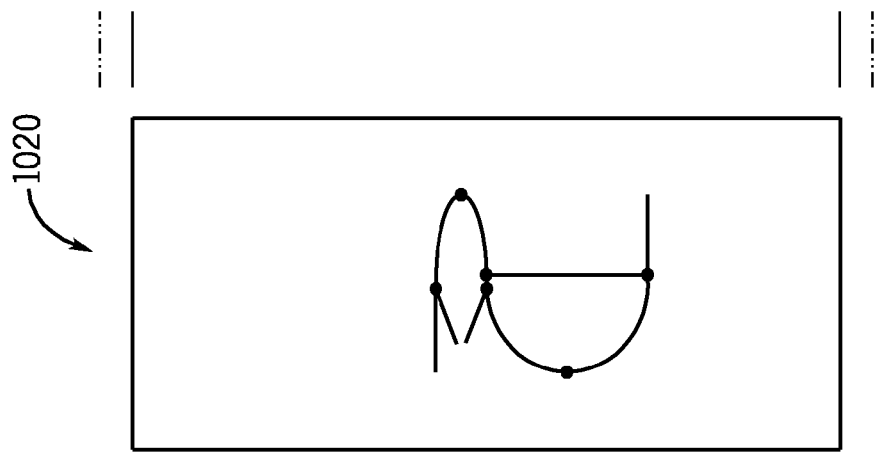
Figure 24A:
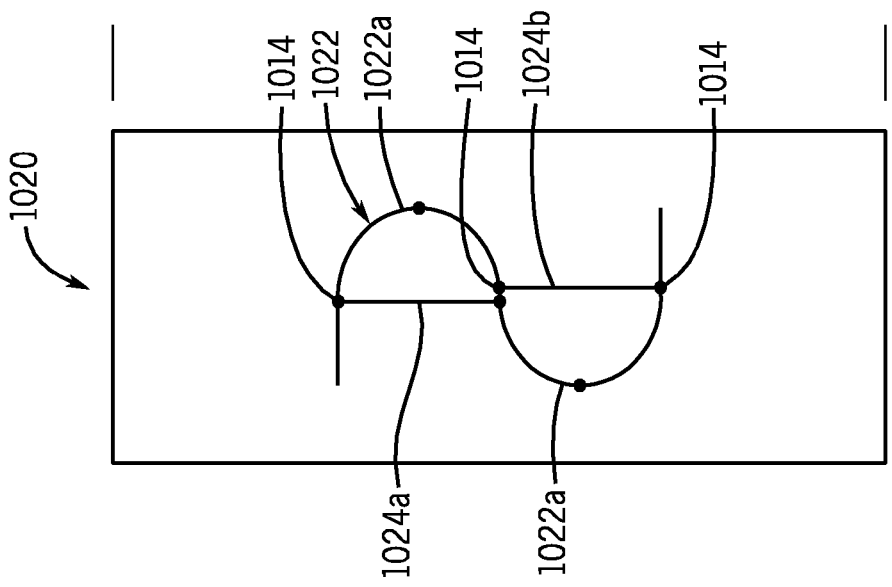

One such configuration is shown in FIGS. 24*a*-24*c*, generally referred to as dressing portion 1020. The portion 1020 includes an elastic member 1022 having a complex shape. Such shape can include multiple loops 1022*a*. Although two such loops 1022*a* are provided, one or more than two are also possible. Also, although the elastic member 1020 is shown attached to the dressing portion 1020 (which can be an elastic material, such as a fabric) at least at points 1014 (such as by stitching), the elastic member 1022 can be provided between parts of the dressing portion 1022, such as shown with regard to FIG. 23 and the bars 1018 discussed above can be utilized for the reasons set forth above. Also, although the elastic member 1022 is shown as an open shape, closed shapes can also be utilized. The loops 1022*a* are each fixed to the dressing portion 1022 to restrain the same in a first shape such that when the restraint is removed, each of the loops move towards a second shape which either tend to open or close a wound over which the dressing portion 1022 is applied (such as with an adhesive, as discussed above). Although the embodiment of FIGS. 24*a*-24*c* is described with regard to closing a wound, the elastic members can be configured to tend to open the wound. Furthermore, some of the loops 1022*a* can be configured for closing the wounds, while others configured to open the wound.

A restraining member 1024*a*, 1024*b* is provided between each loop 1022*a*, which when removed, such as by cutting or otherwise severing the same, removes the restraint on the loop 1022*a* and tends to close the loop (in the illustrated embodiment). In the configuration illustrated in FIGS. 24*a*-24*c*, the restraining members 1024*a* are rigid, As shown in FIG. 24*b*, when the restraining member 1024*a* is removed, such as by cutting, loop 1022*a* (at the top of the page) becomes smaller which reduces the length of the dressing portion 1020 to trend to close the wound. If additional closure is desired, restraining member 1024*b* can be removed from the lower loop 1022*a*, such as by cutting, to further reduce the length of the dressing portion 1020 as shown in FIG. 24*c*. Any number of such loops 1022*a* can be provided to selectively stepwise close or open the wound, as needed.

An alternative configuration of the dressing portion of FIGS. 24*a*-24*c* is shown in FIGS. 24*d* and 24*e* and generally referred to by reference numeral 1020*a* in which like reference numerals are used for like features. In the configuration of FIGS. 24*d* and 24*e*, a flexible restraining member is used, such as a string, which is fixed to the elastic member 1022 at one end and to the dressing portion 1020*a* at another end. The restraining member 1024 is cut or otherwise severed or removed to remove the restraint from the loops 1022*a* (there such loops 1022*a* are shown by way of example in FIGS. 24*d* and 24*e*). In the configuration of FIGS. 24*d* and 24*e*, a restraining member (1024*c*) is used for each leg of the loop 1022*a*. Thus, restraining members 1024*c*1 and 1024*c*2 are cut to remove the restraint from the top loop 1022*a* (and partially remove the restraint from the middle loop 1022*a*), as shown in FIG. 24*e*. Restraining members 1024*c*3 and 1024*c*4 can also be cut to remove the restraint from the bottom loop 1022*a* (and to remove the remaining restraint from the middle loop 1022*a*), Additional loops 1022*a* may be provided.

Figure 25A:
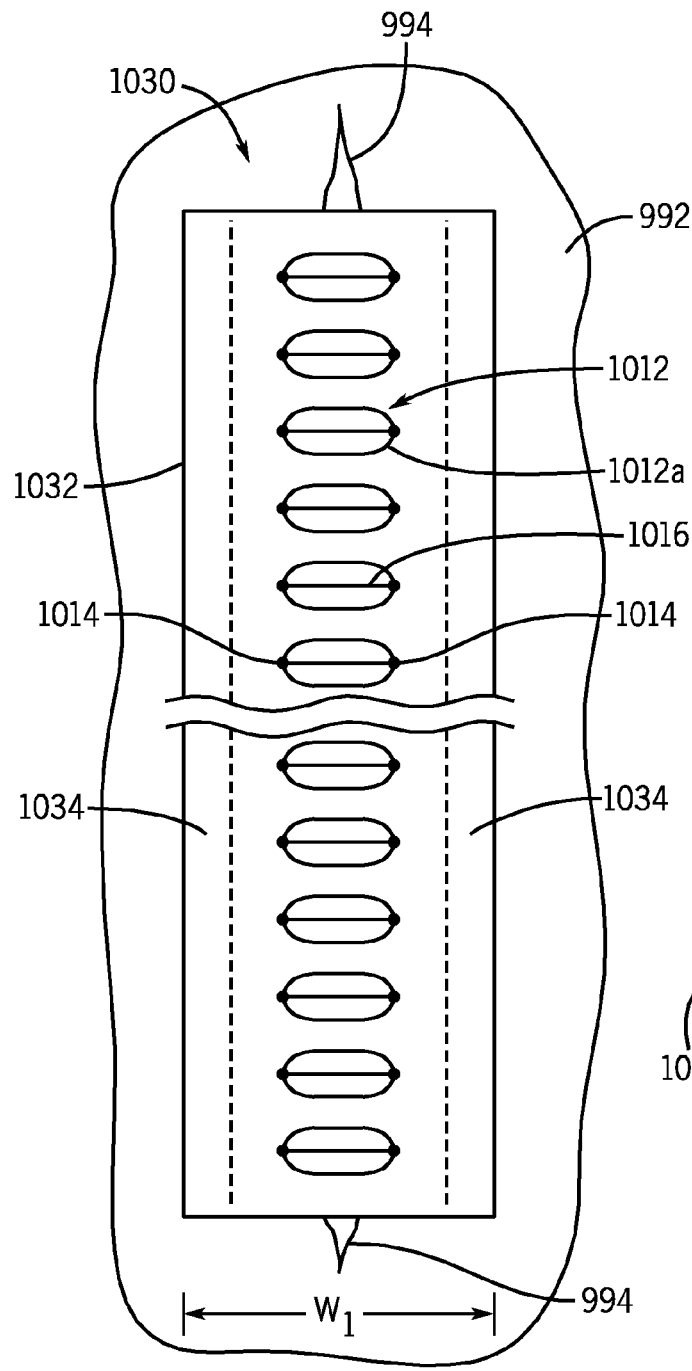
FIGS. 25a and 25b illustrate another alternative dressing portion in which multiple elastic members are provided along a length of the wound.
Figure 25B:
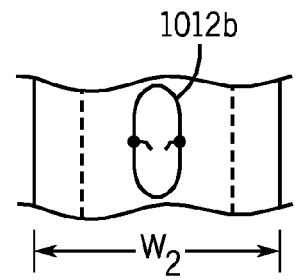

Referring now to FIGS. 25*a* and 25*b*, there is shown another embodiment of a dressing, generally referred to by reference numeral 1030. The dressing includes a portion 1032 for covering the wound, which is flexible, such as an elastic material or fabric. On a side of the portion 1032 that faces the skin 992, an adhesive 1034 is applied, such as along a peripheral edge of the portion 1032. Release layers (not shown) are also provided, as discussed above, over the adhesive 1034 and removed when the portion 1032 is to be adhered to the skin 992. The portion 1032 includes a plurality of elastic members, such as elastic member 1012 configured as shown and described in FIGS. 20*a* and 20*b* along a length of the dressing 1030. The elastic members 1012 are configured such that removing a restraint thereon tends to close a wound 994 over which it is applied in the width direction. Thus, as shown in FIG. 25*b*, when the restraint is removed, such as by cutting the restraining member(s) 1016, a corresponding part of the portion 1032 changes shape from a first width W1 to a smaller width W2. Dressing 1032 is particularly useful for longer wounds. As shown in FIG. 20*e*, each of the elastic members 1012 may be provided with more than one restraining member such that the amount of closure (change in width) can be varied over the length L of the dressing 1032, which may be particularly useful for wounds that may be irregular in that the amount of closure necessary may vary over the length of the wound. Such dressing may be configured in any of the ways discussed above, such as opening a wound.

Figure 25C:
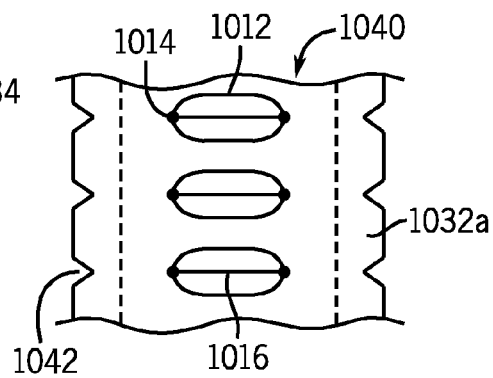
FIGS. 25c and 25d illustrate an alternative dressing portion of FIGS. 25a and 25b.
Figure 25D:
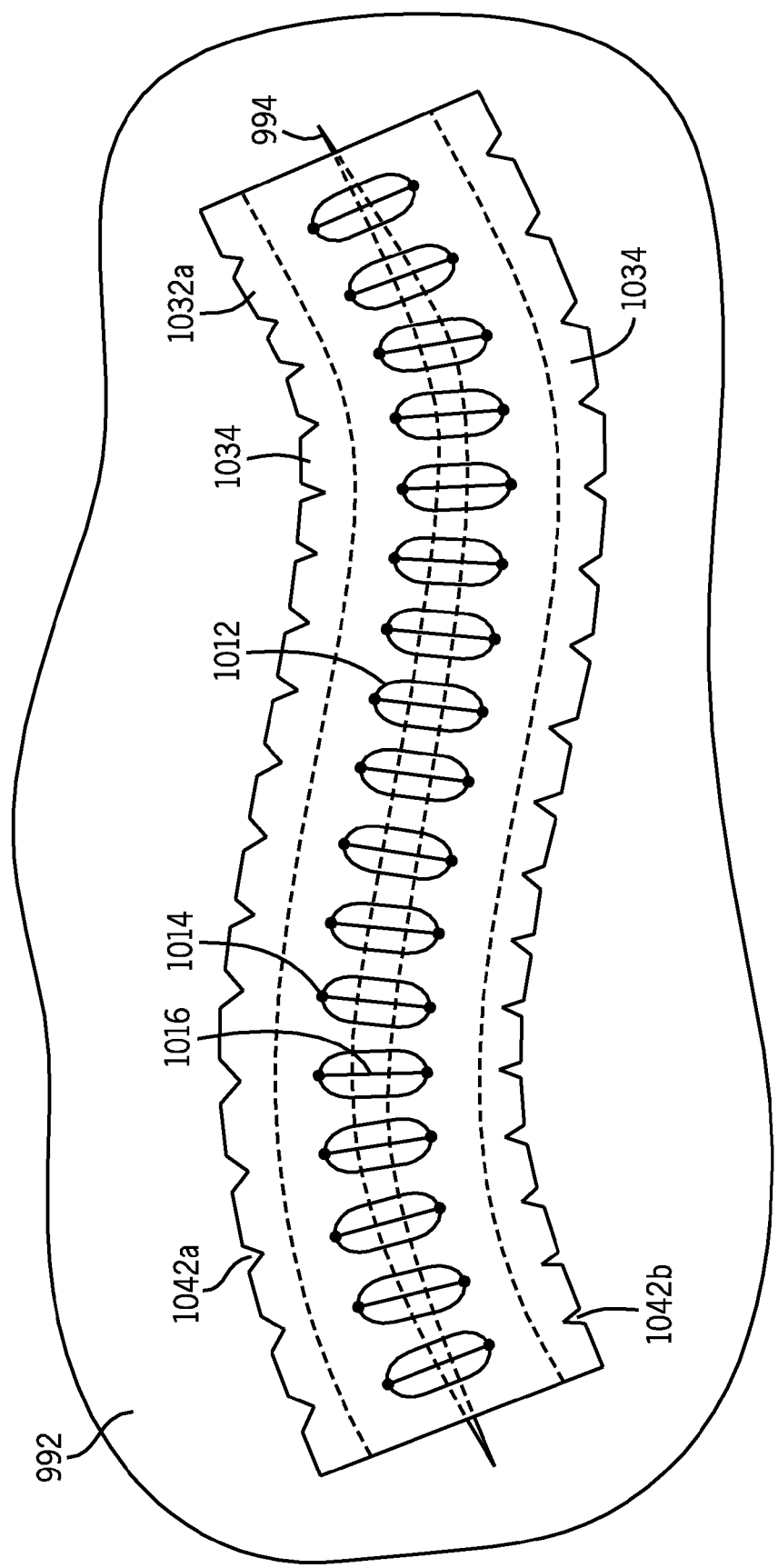

Referring now to FIGS. 25*c* and 25*d*, there is shown a variation of the dressing 1030 shown in FIGS. 25*a* and 25*b*, such dressing being generally referred to by reference numeral 1040 and in which like reference numerals refer to like features. As shown in FIG. 25*c*, the dressing 1040 includes an edge that facilitates curving the portion 1032*a*, such as a series of notches 1042. Other means of facilitating curvature of the portion 1032*a*, such as a series of slits or additional elasticity of the portion 1032*a* at the edges may also be used. as shown in FIG. 25*d*, the portion 1032*a* can be easily curved and applied over an irregularly shaped (non-linear) wound 994 by opening some of the notches 1042*a* and closing others 1042*b*.

The dressings 1030 and 1040 can be provided in large lengths, such as on a roll, and cut to the desired length. Although many of the dressings shown above are shown with a portion of the wound 994 extending past a periphery of the dressing, such is shown so as to illustrate a closure of the wound. Those skilled in the art will appreciate that the dressing can completely cover the extent of the wound.

Furthermore, although the dressing described above are discussed with regard to closing or opening a wound, such a use is not necessary. For example, the dressing may have utility for other uses for applying an elongating or reducing pressure on the skin. For example, the dressing can apply an elongating pressure, particularly incrementally over time, to stretch the skin in advance of a surgical procedure in which extra skin is necessary, such as to provide extra skin that is excised for other portions of the body, such as burned portions. In such an exemplary procedure, the dressing will be less traumatic than conventional skin stretching procedures which require an implant of an expanding device.

Although used for purposes other than dressing a wound, the dressing will still be referred as such (i.e., as a dressing although capable of other uses).

Referring now to FIGS. 26a-26f, there are shown two additional embodiments of a dressing, generally referred to by reference numerals 1050 and 1100, respectively. A first of such embodiments is shown in FIGS. 26b and 26e, a second of such embodiments being shown in FIGS. 26c and 26f, with FIGS. 26a and 26d being common to each of the two embodiments.

Referring first to FIG. 26a, the dressing 1050, 110 includes an adhesive ring portion 1052 formed of a material, such as plastic film or woven fabric and having an adhesive 1054 on a surface corresponding to a surface contacting the skin 1056 around a wound, such as a puncture wound 1058. A first elastic member 1060a, 1060b is formed in a first shape, such as having a convex (slightly cured away from the skin/adhesive) shape 1060a or concave (slightly curved towards the skin/skin adhesive) shape 1060b and attached to the adhesive ring 1054, by any means known in the art, such as by stitching, adhering, heat welding etc. The first elastic member is capable of being deformed into a second shape, such as those shown in FIGS. 26b and 26c by a second elastic member 1062. The second elastic member is fixed to the dressing, such as around an inner periphery of the adhesive ring 1054 at a free end 1062a, such as by adhering, stitching, stapling, clipping, heat welding or the like. The second elastic member 1062 is restrained into a shape, such as shown in FIG. 26a by a restraining member 1064, which can be a rigid member fixed to the second elastic member at at least two points, such as by adhering or the like. Such restraining member 1064 can also be integrally formed with the second elastic member 1062. Thus, the restraining member 1064 restrains the second elastic member 1062 into a shape that further restrains the first elastic member 1060a, 1060b into the first shape, as shown in FIGS. 26b and 26c. Alternatively, restraining members can be used to restrain each of the first elastic member 1060a, 1060b and second elastic member 1062 and additional restraint can be used to restrain the first elastic member 1060a, 1060b in its restrained shape (such as by releasably fixing a lower surface of the restraining member 1064 to an upper surface of the first elastic member 1060a, 1060b.

When the restraint is removed, such as by cutting or otherwise severing the restraining member 1064, the restraining member 1064 coils up on itself such that its diameter is reduced, thereby removing restraint from the first elastic member 1060a, 1060b to both reduce the diameter of the dressing from D1 to D2 and to cup the first elastic member 1060a, 1060b either upwards from the skin 1056, as shown in FIG. 26e, or downwards into the skin 1056, as shown in FIG. 26f. Thus, the reduction in diameter applies a pressure to the wound to close the same, as shown in FIGS. 26e and 26f and the cupping of the first elastic member 1060a, 1060b additionally either provides a sealed evacuated environment for the wound (which could be cut, puncture or a blister 1058a caused by a thermal or chemical burn), as shown in FIG. 26e, or apply pressure to the wound to stop bleeding, as shown in FIG. 26f. Where the first elastic member 1060a cups upward, the second elastic member 1062 can be configured with a larger diameter such that its unrestrained shape (see FIG. 26d) does not interfere with the upward movement of the first elastic member 1060a. After the dressing 1050, 1100 is applied to the skin and the restraining member 1064 is removed, such as by cutting, it can be fully removed from the dressing, such as by cutting it off at its ends or breaking the same at its ends, such as by providing a weakened portion at the ends that facilitate breaking. Also, the second elastic member 1062 can also be fully removed from the dressing after its restraint is removed and the first elastic member takes its desired shape, such as by removing the fixation of the first elastic member.

The dressings 1050, 1100 can be configured with any of the features and for any uses discussed in co-pending U.S. application Ser. No. 13/008,881 filed on Jan. 18, 2011, the entire contents of which is incorporated herein by reference.

Referring now to FIGS. 27a-27c, there is shown an embodiment of a dressing which adds one or more elastic members to the dressing of FIGS. 18a-18c, such as that illustrated in FIGS. 20a and 20b. Like reference numerals in FIGS. 27a-27c indicate like features to those shown in FIGS. 18a-18c, 20a and 20b. The dressing 992a is applied as described with regard to FIGS. 18a-18c. However, one or more elastic members, such as the one described with regard to FIGS. 20a and 20 and indicated by reference numeral 1012 is provided. Therefore, as shown in FIG. 24b, if the dressing does not fully close the wound 994, or if the wound 994 needs extra closing after time (e.g., during the healing process such as after swelling subsides), the elastic members 1012 can be closed to provide any additional closure to the wound, as shown in FIG. 27c. Similarly, the elastic member can be configured to opening the wound or otherwise providing an enlarging pressure to the skin.

The portions disclosed above may be elastic, inelastic or partly elastic, and can be configured to conform to the changes in the configuration of aforementioned elastic members.

Any of the portions shown in FIGS. 20e-27 can be configured to change shape by elongating or enlargement (as shown in FIGS. 20c and 20d) instead of by reducing in length in the direction S.

Although the restraining members 1016, 1016b, 1016c are described above as being cut or severed, they can be released from restraining the elastic members in different ways, such as being glued or otherwise attached to the elastic member at various points 1014 and such attachment being disconnected, such as by pulling the restraining member(s) or a portion attached thereto to break the attachment.

The elastic members in any of the embodiments discussed above can also be cut or otherwise severed after they take their unrestrained shape if it is desired that the application of force resulting from the elastic member(s) is no longer desired. Such cutting can be along a cross-sectional area thereof or such elastic members can be broken along a cross-section portion, such as at a weakened portion. The weakened portion can be of any type known in the art, such as by providing a perforated portion or a reduced cross-sectional area portion to facilitate the breaking.

The elastic members discussed above, may be provided in any material, shape, configuration and attachment to the dressing portion such that it deforms from a first shape to a second shape for a desired effect. Some examples of materials are plastics capable of elastic deformation and metals capable of elastic deformation, such as spring steels. Examples of shapes of the elastic members are discussed above but is not exhaustive of the possible shapes, sizes and configurations of the elastic members that can be utilized for any given desired effect. The elastic members can be fixed to a surface of the dressing portion, such as by stitching or adhering, at at least enough points to provide the desired effect brought about by the shape change when the preloading of the elastic member is released by releasing a restraint which maintains the elastic member in the preloaded shape. The elastic member can also be formed at least partially integrally with the dressing portion, such as being embossed into the dressing portion or embossed with an interior insert of a material capable of elastic deformation. The elastic members can also be formed inside the dressing portions, such as by being woven in an interior of the dressing portion.

Any of the dressings described above may be provided with a medicament, such as for promoting healing, reducing inflammation, fighting infection etc.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A dressing for application to skin, the dressing comprising:
    a bandage comprising an elastic material;
    an adhesive applied on at least a portion of a first surface of the bandage for adhering the bandage to the skin;
    an elastic member attached to a second surface of the bandage at at least first and second points to restrain the elastic member into a first shape, the first shape being elongated in a first direction such that a dimension of the elastic member in the first direction is longer than a dimension of the elastic member in a second direction, the second direction being offset from the first direction, the first and second surfaces being opposing surfaces, the elastic member being capable of being deformed into the first shape and elastically returning towards an unrestrained second shape, the second shape being elongated in the second direction such that a dimension of the elastic member in the second direction is longer than a dimension of the elastic member in the first direction; and
    a restraining member fixed to the elastic member at at least third and fourth points such that the restraining member is held in one of compression or tension to maintain the elastic member in the first shape by tending to keep the at least two points from moving closer or further away from each other, respectively;
    wherein the at least first and second points are located at different positions relative to the at least third and fourth points; and
    when the restraining member is removed from restraining the elastic member, the elastic member moves towards the unrestrained second shape to one or more of elongate or reduce a dimension of the elastic material of the bandage to apply a pressure to corresponding portions of the skin.

2. The dressing of claim 1, wherein the bandage has a rectangular shape.

3. The dressing of claim 2, wherein the adhesive is applied to the first surface of the bandage at first and second ends of the rectangular shape.

4. The dressing of claim 3, wherein the first and second ends are separated in a lengthwise direction.

5. The dressing of claim 3, wherein the first and second ends are separated in a widthwise direction.

6. The dressing of claim 1, wherein the bandage is constructed of first and second portions, each having the adhesive applied on the first surface for adhering the first and second portions to the skin.

7. The dressing of claim 1, wherein the portion includes portions for facilitating application of the portion to the skin in a non-linear shape.

8. The dressing of claim 7, wherein the portions comprise a series of notches disposed at one or more of an edge of the portion.

9. The dressing of claim 1, wherein the elastic member is configured so as to reduce or enlarge the dimension in one or more of a width or length of the bandage.

10. The dressing of claim 1, wherein the elastic member comprises two or more elastic members.

11. The dressing of claim 10, wherein the two or more elastic members are arranged in one or more of a width direction or a length direction of the portion.

12. The dressing of claim 10, wherein at least one of the two or more elastic members is arranged interiorly of another of the two or more elastic members.

13. The dressing of claim 1, wherein the elastic member has a closed shape when viewed in a direction from the second surface towards the first surface.

14. The dressing of claim 1, wherein the elastic member has an open shape.

15. The dressing of claim 1, wherein the elastic member has a complex shape.

16. The dressing of claim 1, wherein the elastic member is attached to a surface of the portion.

17. The dressing of claim 1, wherein the elastic member is formed interiorly to the portion.

18. The dressing of claim 1, wherein the elastic member is at least partially formed integrally with the portion.

19. The dressing of claim 1, wherein the restraining member is a tensile member.

20. The dressing of claim 19, wherein the tensile member is one or more of a flexible or rigid member.

21. The dressing of claim 1, wherein the restraining member is a rigid compressive member.

22. The dressing of claim 1, wherein the restraining member comprises two or more restraining members, each connected to the elastic member.

23. The dressing of claim 1, wherein the two or more restraining members are configured such that removal of each one incrementally moves the elastic element from the first shape towards the second shape through one or more intermediate shapes.

24. The dressing of claim 1, wherein the two or more restraining members has one or more of a differing length or elasticity.

25. The dressing of claim 1, wherein the portion includes one or more rigid portions for facilitating the elongation or reduction in the dimension over a width of the portion.

26. The dressing of claim 25, wherein the one or more rigid portions comprise a bar.

27. The dressing of claim 25, wherein the one or more rigid portions comprise an embossed part of the portion.

28. The dressing of claim 1, wherein the elastic material comprises an elastic woven material having one or more of weft and warp fibers being elastic.

29. The dressing of claim 1, wherein the elastic member is a second elastic member and the portion is formed at least partially of a first elastic member restrained into a shape in which the portion is applied to the skin.

30. The dressing of claim 29, wherein the restraining member restrains both the first and second elastic members.

* * * * *